US010294287B2

(12) United States Patent
Greve

(10) Patent No.: US 10,294,287 B2
(45) Date of Patent: May 21, 2019

(54) MOLECULES THAT SELECTIVELY ACTIVATE REGULATORY T CELLS FOR THE TREATMENT OF AUTOIMMUNE DISEASES

(71) Applicant: Delinia, Inc., Emeryville, CA (US)

(72) Inventor: Jeffrey Greve, Berkeley, CA (US)

(73) Assignee: Delinia, Inc., Emeryville, CA (US)

( * ) Notice: Subject to any disclaimer, the term of this patent is extended or adjusted under 35 U.S.C. 154(b) by 0 days.

(21) Appl. No.: 15/696,811

(22) Filed: Sep. 6, 2017

(65) Prior Publication Data
US 2018/0037624 A1 Feb. 8, 2018

Related U.S. Application Data

(63) Continuation of application No. 15/002,144, filed on Jan. 20, 2016, now abandoned.

(51) Int. Cl.
A61K 38/20 (2006.01)
C07K 14/55 (2006.01)
G01N 33/50 (2006.01)
A61K 38/00 (2006.01)

(52) U.S. Cl.
CPC .......... *C07K 14/55* (2013.01); *G01N 33/505* (2013.01); *A61K 38/00* (2013.01); *C07K 2319/30* (2013.01)

(58) Field of Classification Search
CPC ..................................................... C07K 14/55
See application file for complete search history.

(56) References Cited

U.S. PATENT DOCUMENTS

| | | | |
|---|---|---|---|
| 4,853,332 A | 8/1989 | Mark et al. | |
| 4,902,502 A | 2/1990 | Nitecki et al. | |
| 5,089,261 A | 2/1992 | Nitecki et al. | |
| 5,206,344 A | 4/1993 | Katre et al. | |
| 5,281,698 A | 1/1994 | Nitecki | |
| 5,466,447 A | 11/1995 | Abels et al. | |
| 5,650,150 A | 7/1997 | Gillies | |
| 6,348,192 B1 | 2/2002 | Chan et al. | |
| 6,541,610 B1 | 4/2003 | Smith | |
| 6,602,498 B2 | 8/2003 | Shen | |
| 6,689,353 B1 | 2/2004 | Wang et al. | |
| 6,911,197 B2 | 6/2005 | Shen | |
| 6,927,043 B2 | 8/2005 | Chan et al. | |
| 6,955,807 B1 | 10/2005 | Shanafelt et al. | |
| 7,105,653 B2 | 9/2006 | Shanafelt et al. | |
| 7,148,321 B2 | 12/2006 | Gillies et al. | |
| 7,186,804 B2 | 3/2007 | Gillies et al. | |
| 7,371,371 B2 | 5/2008 | Epstein et al. | |
| 7,452,966 B2 | 11/2008 | Glaesner et al. | |
| 7,462,350 B2 | 12/2008 | Gillies et al. | |
| 7,569,215 B2 | 8/2009 | Wittrup et al. | |
| 7,579,439 B2 | 8/2009 | Strom et al. | |
| 7,888,071 B2 | 2/2011 | Gillies et al. | |
| 7,951,360 B2 | 5/2011 | Wittrup et al. | |
| 8,012,465 B2 | 9/2011 | Elias et al. | |
| 8,043,608 B2 | 10/2011 | Gillies et al. | |
| 8,066,994 B2 | 11/2011 | Gillies et al. | |
| 8,124,066 B2 | 2/2012 | Epstein et al. | |
| 8,349,311 B2 | 1/2013 | Wittrup et al. | |
| 8,454,946 B2 | 6/2013 | Shen et al. | |
| 8,765,111 B2 | 7/2014 | Shen | |
| 8,992,902 B2 | 3/2015 | Shen | |
| 8,993,524 B2 | 3/2015 | Bedi et al. | |
| 9,169,350 B2 | 10/2015 | Shen | |
| 9,206,243 B2 | 12/2015 | Leon et al. | |
| 9,289,493 B2 | 3/2016 | Ko | |
| 2004/0171154 A1 | 9/2004 | Storici et al. | |
| 2006/0160187 A1 | 7/2006 | Denis-Mize et al. | |
| 2007/0036752 A1 | 2/2007 | Gillies et al. | |
| 2011/0020266 A1 | 1/2011 | Nissen et al. | |
| 2011/0091412 A1 | 4/2011 | Wittrup et al. | |
| 2011/0150826 A1 | 6/2011 | Paulsen et al. | |
| 2011/0274650 A1 | 11/2011 | Gavin et al. | |
| 2012/0276125 A1 | 11/2012 | Ast et al. | |
| 2013/0195795 A1 | 8/2013 | Gavin et al. | |
| 2014/0004080 A1 | 1/2014 | Klatzmann et al. | |
| 2014/0044675 A1 | 2/2014 | Hosse et al. | |
| 2014/0046026 A1 | 2/2014 | Garcia et al. | |
| 2014/0285898 A1 | 9/2014 | Moliton et al. | |
| 2014/0286898 A1 | 9/2014 | Gavin et al. | |
| 2014/0328791 A1 | 11/2014 | Bossard et al. | |
| 2014/0343252 A1 | 11/2014 | Gavin et al. | |
| 2015/0017120 A1 | 1/2015 | Wittrup et al. | |
| 2015/0132254 A1 | 5/2015 | Wittrup et al. | |
| 2015/0218260 A1 | 8/2015 | Klein et al. | |
| 2015/0335669 A1 | 11/2015 | Chae et al. | |
| 2015/0374788 A1 | 12/2015 | Paulsen et al. | |
| 2016/0083514 A1 | 3/2016 | Shen | |
| 2016/0090407 A1 | 3/2016 | Hosse et al. | |
| 2016/0208017 A1 | 7/2016 | Ast et al. | |
| 2016/0263240 A1 | 9/2016 | Ast et al. | |

FOREIGN PATENT DOCUMENTS

| | | |
|---|---|---|
| CN | 102174111 A | 9/2011 |
| CN | 103193887 A | 7/2013 |
| EP | 1370280 A2 | 12/2003 |
| EP | 1076704 B1 | 1/2007 |
| EP | 1454138 A4 | 2/2007 |
| EP | 1688146 B1 | 7/2007 |
| EP | 2288372 B1 | 2/2012 |

(Continued)

OTHER PUBLICATIONS

Altschul, et al., Basic local alignment search tool., Oct. 1990, J. Mol. Biol. 215:403-410, doi:10.1016//S0022-2836(05)80360-2.

(Continued)

*Primary Examiner* — Prema M Mertz
(74) *Attorney, Agent, or Firm* — McCarter & English, LLP

(57) ABSTRACT

This invention provides for a fusion protein between an IL2αβγ Selective Agonist protein (IL2 Selective Agonist) and a IgG Fc protein using a linker. The IL2 Selective Agonist moiety provides a therapeutic activity by selectively activating the IL2αβγ form of the receptor, thus selectively stimulating Tregs. The Fc moiety provides a prolonged circulating half-life compared to the circulating half-life of IL-2 or an IL2SA protein.

13 Claims, 15 Drawing Sheets

Specification includes a Sequence Listing.

(56) References Cited

FOREIGN PATENT DOCUMENTS

| | | |
|---|---|---|
| WO | 90/00565 | 1/1990 |
| WO | 1995-008340 | 3/1995 |
| WO | 1999-043713 | 9/1999 |
| WO | 1999-060128 | 11/1999 |
| WO | 2005-014642 A2 | 2/2005 |
| WO | 2010-085495 A1 | 7/2010 |
| WO | 2011109789 A2 | 9/2011 |
| WO | 2012107417 A1 | 8/2012 |
| WO | 2012-146628 A1 | 11/2012 |
| WO | 2014023752 A1 | 2/2014 |
| WO | 2014145907 A1 | 9/2014 |
| WO | 2014-201378 A1 | 12/2014 |
| WO | 2015-164815 A1 | 10/2015 |
| WO | 2016014428 A2 | 1/2016 |
| WO | 2016-025645 A1 | 2/2016 |
| WO | 2016-025647 A1 | 2/2016 |
| WO | 2016025385 A1 | 2/2016 |
| WO | 2016-057651 A1 | 4/2016 |

OTHER PUBLICATIONS

Altschul et al., Gapped BLAST and PSI-BLAST: a new generation of protein database search programs., Nucleic Acids Res., 1997 25(17):3389-3402.

Argos, An investigation of oligopeptides linking domains in protein tertiary structures and possible candidates for general gene fusion., 1990, J Mol. Biol. 211:943-58, doi:10.1016/0022-2836(90)90085-Z.

Atkins, et al., Hypothyroidism after treatment with interleukin-2 and lymphokine-activated killer cells, N Engl. J. Med, Jun. 16, 1988, 318(24):1557-63.

Batzer, et al., Enhanced evolutionary PCR using oligonucleotides with inosine at the 3'-terminus, Nucleic Acid Res., 1991, 19:5081.

Bell, et al., Sustained in vivo signaling by long-lived IL-2 induces prolonged increases of regulatory T cells., J Autoimmunity, Jan. 2015, 56:66-80.

Calissano, et al., In vivo site-directed mutagenesis of Neurospora crassa beta-tubulin gene by spheroplasts transformation with oligonucleotides, 1996, Fungal Genet. Newsletter 43: 15-16.

Cantrell, et. al, The interleukin-2 T-cell system: a new cell growth model Jun. 22, 1984, Science, 224:1312-1316, DOI: 10.1126/science.6427923.

Cassell, et. al., Therapeutic Enhancement of IL-2 Through Molecular Design, 2002, Curr Pharm Des., 8:2171-83.

Chen, et al., IL-2 Controls the Stability of Foxp3 Expression in TGF-β-Induced Foxp3+ T Cells In Vivo, 2011, J Immunol, 186:6329-37.

Chen et al., Fusion protein linkers: Property, design and functionality., Adv. Drug Delivery Rev.., Oct. 2013, 65(10):1357-69.

Chianese-Bullock, et al., Autoimmune toxicities associated with the administration of antitumor vaccines and low-dose interleukin-2, J Immunother, Jul.-Aug. 2005, 28(4):412-9.

Co-pending U.S. Appl. No. 15/002,144, filed Jan. 20, 2016.

Co-pending U.S. Appl. No. 15/265,764, filed Sep. 14, 2016.

Co-pending U.S. Appl. No. No. 15/265,770, filed Sep. 14, 2016.

Czajkowsky, et al., Fc-fusion proteins: new developments and future perspectives., 2012; EMBO Mol Med. 4(10):1015-28 DOI 10.1002/emmm.201201379.

Dauphinee, et al., Interleukin 2 deficiency is a common feature of autoimmune mice, J Immunology, Dec. 1981, 127(6):2483-7.

Davey et al., Safety, Tolerability, Pharmacokinetics, and Efficacy of an Interleukin-2 Agonist Among HIV-Infected Patients Receiving Highly Active Antiretroviral Therapy., Feb. 16, 2008, J Cytokine Res. 28(2): 89-100. doi:10.1089/jir.2007.0064.

Dunmont et, al., Impact on Pharmacokinetic and Biological Activity of Protein Therapeutics., May 2006, BioDrugs 20(3):151-60 DOI: 10.2165/00063030-200620030-00002.

Furtado, et al., Interleukin 2 signaling is required for CD4+ regulatory T cell function, JEM, Sep. 16, 2002, 196(6):851-857.

Gilles, et al., Antibody-targeted interleukin 2 stimulates T-cell killing of autologous tumor cells., Immunology, Feb. 1992, Proc Natl Acad Sci, 89:1428-32.

Gillies et al., Improved Circulating Half-Life and Efficacy of an Antibody-Interleukin 2 Immunocytokine Based on Reduced Intracellular Proteolysis., Jan. 2002, Clinical Cancer Res., 8:210-6.

Hecht, et al., Rationale-Based Engineering of a Potent Long-Acting FGF21 Analog for the Treatment of Type 2 Diabetes., PLOS One, 7(11):e49345, Published: Nov. 27, 2012 • http://dx.doi.org/10.1371/journal.pone.0049345.

Huanget, et al., Restoration of an early, progressive defect in responsiveness to T-cell activation in lupus mice by exogenous IL-2, Autoimmunity, 1993;15(1):19-29.

International Search Report dated Jan. 29, 2016 for PCT-US15-041177.

International Search Report dated Dec. 8, 2015 for PCT/US2015/044462.

Jailwala, et al., Apoptosis of CD4+CD25 high T Cells in Type 1 Diabetes May Be Partially Mediated by IL-2 Deprivation, Aug. 2009, PLOS One. 2009; 4:e6527, 1-13.

Karlin, et al., Methods for assessing the statistical significance of molecular sequence features by using general scoring schemes, Proc. Natl. Acad. Sci. USA, 1990, 87:22264.2268.

King et al., Phase I Clinical Trial of the Immunocytokine EMD 273063 in Melanoma Patients., J. Clinical Oncology, Nov. 15, 2004, 22:4463-73.

Kirchner, et al., Pharmacokinetics of recombinant human interleukin-2 in advanced renal cell carcinoma patients following subcutaneous application.,Jul. 1998, 46:5-10, 10.1046/j.1365-2125.1998.00036.x.

Kitas, et al., Deficient interleukin 2 production in rheumatoid arthritis,association with active disease and systemic complications, Bacon PA. Clin Exp Immunol. Aug. 1988;73(2):242-9.

Klatzmann, et al., The promise of low-dose interleukin-2 therapy for autoimmune and inflammatory diseases., Apr. 17, 2015, Nat Rev Immunol, 15:283-94.

Koreth, et al., Interleukin-2 and Regulatory T Cells in Graft-versus-Host Disease., Dec. 1, 2011, New Engl. J Med., 365(2):2055-66.

Kren et al., In vivo site-directed mutagenesis of the factor IX gene by chimeric RNA/DNA oligonucleotides., Nat Med. Nature Med 4, 1998 285-290 doi:10.1038/nm0398-285.

Kroemer et al., The role of interleukin 2 in autoimmunity, Immunol Today, Jul. 1989, 10(7):246-51.

Liston, et. al., Tracing the action of IL-2 in tolerance to islet-specific antigen, Immunology and Cell Biology (2007) 85, 338-342.

Liu, et al., A Novel Antibody Engineering Strategy for Making Monovalent Bispecific Heterodimeric IgG Antibodies by Electrostatic Steering Mechanism, J Biol Chem., Mar. 20, 2015, 290:7535-62.

Long, et al., Defects in IL-2R Signaling Contribute to Diminished Maintenance of FOXP3 Expression in CD4 CD25 Regulatory T-Cells of Type 1 Diabetic Subjects., Feb. 2010, Diabetes 59;407-15.

Mahmud, et al., Interleukin-2 and STAT5 in regulatory T cell development and function, JAK-STAT, Published online: Jan. 1, 2013, 2:1, e23154, 1-7.

Malek, et al., CD4 regulatory T cells prevent lethal autoimmunity in IL-2Rbeta-deficient mice: Implications for the nonredundant function of IL-2, Immunity, Aug. 2002, 17(2):167-78.

Malek, et al., Interleukin-2 Receptor Signaling: At the Interface between Tolerance and Immunity, 2010, Immunity, 33: 153-65.

Malek, et al., Tolerance, not immunity, crucially depends on IL-2, Nat Rev Immunol. Sep. 2004, 4(9):665-74.

Margolin, et al., Phase I Trial of BAY 50-4798, an Interleukin-2Specific Agonist in Advanced Melanoma and Renal Cancer, Clin Cancer Res., Jun. 1, 2007, 13:3312-9.

Moschos, et al., Focus on FOCIS: interleukin 2 treatment associated autoimmunity, Clin Immunol, May 2008,127(2):123-9. doi: 10.1016/j.clim.2008.02.011.

Myszka, et al., Kinetic analysis of ligand binding to interleukin-2 receptor complexes created on an optical biosensor surface, Protein Sci, 1996, 5:2468-78.

(56) References Cited

OTHER PUBLICATIONS

Oganesyan, et al., 2008, Structural characterization of a human Fc fragment., Acta Crystallogr D (2008), Biol Crystallography, 64:700-704 doi:10.1107/S0907444908007877.

Ohtsuka, et al., An alternative approach to deoxyoligonucleotides as hybridization probes by insertion of deoxyinosine at ambiguous codon positions, Mar. 10, 1985, J. Biol. Chem. 260:2605-208.

Penichet, et al., Antibody-IL-2 fusion proteins: A novel strategy for immune potentiation., J Human Antibodies, 1997 8(1):106-118.

Poli, et al., CD56 bright natural killer (NK) cells: an important NK cell subset, Immunology 2009, 126, 458-465.

Prometheus Laboratories Inc., PROLEUKIN® (aldesleukin) for intravenous infusion. Available at http://www.proleuldn.com/assets/pdf/proleukin.pdf. Accessed on Oct. 11, 2016.

Rabinovitch, et al., Combination therapy with sirolimus and interleukin-2 prevents spontaneous and recurrent autoimmune diabetes in NOD mice, Diabetes, Mar. 2002, 51(3):638-45.

Ribas et al., Phase I/II open-label study of the biological effects of the interleukin-2 immunocytokine EMD 273063 (hu14.18-IL2) in patients with metastatic malignant melanoma., J Transl Med., Jul. 29, 2009, 7:68.

Ring, et al., Mechanistic and structural insight into the functional dichotomy between IL-2 and IL-15., Oct. 28, 2012, Nat Immunol. 13:1187-95, doi:10.1038/ni.2449.

Rossolini, et al., Use of deoxyinosine-containing primers vs degerate primers for polymerase chain reaction based on ambiguous sequence information., Apr. 1994, Mol. Cell. Probes 8:91-98.

Saadoum, et al., Regulatory T-Cell Responses to Low-Dose Interleukin-2 in HCV-Induced Vasculitis., New Engl. Journal of Med., Dec. 1, 2011, 365:2067-77, Sadlack, et al., Generalized autoimmune disease in interleukin-2-deficient mice is triggered by an uncontrolled activation and proliferation of CD4+ T cells, Eur. J Immunology, Nov. 1995, 25(11):3053-9.

Salfeld, Isotype selection in antibody engineering, Nature Biotechnology, Dec. 2007, 25:1369-72.

Schellenberger, et. al., A recombinant polypeptide extends the in vivo half-life of peptides and proteins in a tunable manner., Nov. 15, 2009, Nat Biot. 27:1186-90.

Schlapschy, et al., Fusion of a recombinant antibody fragment with a homo-amino-acid polymer: effects on biophysical properties and prolonged plasma half-life Jun. 26, 2007, Protein Eng. Des Sel. 20:273-84.

Serreze, et al., Immunostimulation circumvents diabetes in NOD/Lt mice, 1989, J. Autoimmunity, 2:759-776, doi:10.1016/0896-8411(89)90003-6.

Shanafelt, et al., A T-cell-selective interleukin 2 mutein exhibits potent antitumor activity and is well tolerated in vivo., 2000, Nat Biot 18:1197-202 doi:10.1038/81199.

Sleep, et al., Albumin as a versatile platform for drug half-life extension, Biochim Biophys Acta, 2013; 1830:5526-34.

Sondel et al., Current and Potential Uses of Immunocytokines as Cancer Immunotherapy., Antibodies 2012 1 149-171, doi:10.3390/antib1020149.

Steppan, et al., Genome Wide Expression Profiling of Human Peripheral Blood Mononuclear Cells Stimulated With BAY 50/4798, a Novel T Cell Selective Interleukin-2 Analog, J Immunother, Feb./Mar. 2007, 30(2):150-168.

Steppan, et al., Reduced Secondary Cytokine Induction by BAY 50/4796, a High-Affinity Receptor-Specific Interleukin-2 Analog, Journal of Interferon & Cytokine Research, 2006, 26:171-178.

Storici, et al., In vivo site-directed mutagenesis using oligonucleotides, Nature Biotechnology, 2001, 19: 773-776.

Suzuki, et al., Deregulated T cell activation and autoimmunity in mice lacking interleukin-2 receptor beta, Science, Jun. 9, 1995, 268(5216):1472-6.

Tang, et al., Central role of defective interleukin-2 production in the triggering of islet autoimmune destruction, Immunity, 28:687-697. doi:10.1016/ (2008).

Tang, et al., In vitro-expanded antigen-specific regulatory T cells suppress autoimmune diabetes, J. Exp. Med, Jun. 7, 2004, 199(11):1455-65.

Tang, Q., et al, Regulatory T-Cell Therapy in Transplantation: Moving to the Clinic., 2013, Cold Spring Harb, Perspect. Med., 3: 1-15.

Tao et al., Studies of aglycosylated chimeric mouse-human IgG. Role of carbohydrate in the structure and effector functions mediated by the human IgG constant region., J Immunology, Oct. 15, 1989,143(8):2595-2601.

Tian, et al, Accurate multiplex gene synthesis from programmable DNA microchips., Nature 432:1050-1054 doi:10.1038/nature03151.

Wang, et al., Structure of the Quaternary Complex of Interleukin-2 with Its a, β, and γc Receptors., Nov. 18, 2005, Sci. 310:1159-63, DOI: 10.1126/science.1117893.

Weishaupt, et al., The T cell-selective IL-2 mutant AlC284 mediates protection in a rat model of Multiple Sclerosis, J. Neuroimmunol, May 15, 2015, 282:63-72.

Willerford, et al., Interleukin-2 receptor alpha chain regulates the size and content of the peripheral lymphoid compartment, Immunity, Oct. 3, 1995(4):521-30.

You, et al., Adaptive TGF-beta-dependent regulatory T cells control autoimmune diabetes and are a privileged target of anti-CD3 antibody treatment, Proc Natl Acad Sci, Apr. 10, 2007, 104(15):6335-40.

Zheng, et al., Favorably Tipping the Balance between Cytopathic and Regulatory T Cells to Create Transplantation Tolerance., J Immunity, Oct. 19, 2003(4):503-514.

Zheng, et al., IL-2 Receptor-Targeted Cytolytic IL-2/Fc Fusion Protein Treatment Blocks Diabetogenic Autoimmunity in Nonobese Diabetic Mice, J Immunol, 1999, 163:4041-8.

Zhu et al., Remodeling domain interfaces to enhance heterodimer formation., Protein Science (1997), 6781-788.

Zhu, et al., Synergistic Innate and Adaptive Immune Response to Combination Immunotherapy with Anti-Tumor Antigen Antibodies and Extended Serum Half-Life IL-2, Cancer Cell, 2015, 13:27(4):489-501.

Bensinger et al. "Distinct IL-2 Receptor Signaling Pattern in CD4+CD25+Regulatory T Cells", 2004, J Immunol. 172(9): 5287-5296.

Hoffman et al., "Donor-type CD4+CD25+Regulatory T Cells Supress Lethal Acute Graft-Versus-Host Diseases after Allogeneic Bone Marrow Transplantation", 2002, J. Exp. Med. 196(3): 389-399.

Sykes, et al., In Vivo Administration of Interleukin 2 Plus T Cell-Depleted Syngeneic Marrow Prevents Graft-Versus-Host Diseases Mortality and Permits Alloengraftment, The Journal of Experimental Medicine, vol. 171 Mar. 1990 pp. 645-658.

Sykes, et al., Interleukin 2 prevents graft-versus-host disease while preventing the graft-versus-leukemia effect of allogeneic T cells, Proceedings of the National Academy of Sciences, Aug. 1990, vol. 87, pp. 5633-5637.

Zorn et al., IL-2 regulates FOXP3 expression in human CD4+CD25+ regulatory T cells through a STATE-dependent mechanism and induces the expansion of these cells in vivo, Blood, Sep. 1, 2006, vol. 108, No. 5, pp. 1571-1579.

Zorn, et al., Combined CD+ Donor Lymphocyte Infusion and Low-Dose Recombinant IL-2 Expand FOXP3+Regulatory T cells following Allogeneic Hematopoietic Stem Cell Transplantation, Biol Blood Marrow Transplant, Mar. 15, 2009(3), pp. 382-388.

Mikayama et al. Proc. Natl. Acad. Sci. USA (1993) vol. 90, pp. 10056-10060.

Voet et al. Biochemistry John Wiley & Sons, Inc., (1990), pp. 126-128 and 228-234.

Supplementary European Search Report based on co-pending European Patent Application No. 15831523.4, dated Dec. 1,2017—5 pages.

Chen, Sharon A. et al., "Plasma and Lymph Pharmacokinetics of Recombinant Human Interleukin-2 and Polyethylene Glycol-Modified Interleukin-2 in Pigs". Apr. 2000, Journal of Pharmacology and Experimental Therapeutics, vol. 293, No. 1, pp. 248-259.

Katre, Nandini V., et al. "Chemical Modification of Recombinant Interleukin 2 by Polyethylene Glycol Increases its Potency in the Murine Meth a Sarcoma Model", Mar. 1987, Proceedings National Academy of Sciences PNAS vol. 84, No. 6, pp. 1487-1491.

MOLECULES THAT SELECTIVELY ACTIVATE REGULATORY T CELLS FOR THE TREATMENT OF AUTOIMMUNE DISEASES

CROSS-REFERENCE TO RELATED APPLICATIONS

This application is a continuation of U.S. application Ser. No. 15/002,144, filed Jan. 20, 2016, which is incorporated herein by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 127754_90302_Sequence_Listing. The size of the text file is 87 KB, and the text file was created on Aug. 31, 2017.

BACKGROUND OF THE INVENTION

The immune system must be able to discriminate between self and non-self. When self/non-self discrimination fails, the immune system destroys cells and tissues of the body and as a result causes autoimmune diseases, Regulatory cells actively suppress activation of the immune system and prevent pathological self-reactivity and consequent autoimmune disease. Developing drugs and methods to selectively activate regulatory T cells for the treatment of autoimmune disease is the subject of intense research and, until the development of the present invention, has been largely unsuccessful.

Regulatory T cells (Treg) are a class of CD4+CD25+ T cells that suppress the activity of other immune cells. Treg are central to immune system homeostasis, and play a major role in maintaining tolerance to self-antigens and in modulating the immune response to foreign antigens, Multiple autoimmune and inflammatory diseases, including Type 1 Diabetes (T1 D), Systemic Lupus Erythematosus (SLE), and Graft-versus-Host Disease (GVHD) have been shown to have a deficiency of Treg cell numbers or Treg function, Consequently, there is great interest in the development of therapies that boost the numbers and/or function of Treg cells.

One treatment approach for autoimmune diseases being investigated is the transplantation of autologous, ex vivo-expanded Treg cells (Tang, Q., et al, 2013, Cold Spring Harb. Perspect. Med., 3:1-15). While this approach has shown promise in treating animal models of disease and in several early stage human clinical trials, it requires personalized treatment with the patient's own T cells, is invasive, and is technically complex. Another approach is treatment with low dose interleukin-2 (IL-2). Treg cells characteristically express high constitutive levels of the high affinity IL-2 receptor, IL2Rαβγ, which is composed of the subunits IL2RA (CD25), IL2RB (CD122), and IL2RG (CD132), and Treg cell growth has been shown to be dependent IL-2 (Malek, T. R., et al., 2010, Immunity, 33:153-65). Clinical trials of low-dose IL-2 treatment of chronic GVHD (Koreth, et al., 2011, N Engl Med., 365:2055-66) and HCV-associated autoimmune vasculitis patients (Saadoum, D., et al., 2011, N Engl Med., 365:2067-77) have demonstrated increased Treg levels and signs of clinical efficacy. New clinical trials investigating the efficacy of IL-2 in multiple other autoimmune and inflammatory diseases have been initiated.

Proleukin (marketed by Prometheus Laboratories, San Diego, Calif.), the recombinant form of IL-2 used in these trials, is associated with high toxicity, Proleukin is approved for the treatment of Metastatic Melanoma and Metastatic Renal Cancer, but its side effects are so severe that its use is only recommended in a hospital setting with access to intensive care (http://www.proleukin.com/assets/pdf/proleukin.pdf). Until the more recent characterization of Treg cells, IL-2 was considered to be immune system stimulator, activating T cells and other immune cells to eliminate cancer cells. The clinical trials of IL-2 in autoimmune diseases have employed lower doses of IL-2 in order to target Treg cells, because Treg cells respond to lower concentrations of IL-2 than many other immune cell types because of their expression of IL2Rαβγ (Klatzmann D, 2015 Nat Rev Immunol. 15:283-94). However, even these lower doses resulted in safety and tolerability issues, and the treatments used have employed daily subcutaneous injections, either chronically or in intermittent 5 day treatment courses. Therefore, there is need for an autoimmune disease therapy that potentiates Treg cell numbers and function, that targets Treg cells more specifically than IL-2, that is safer and more tolerable, and that is administered less frequently.

One approach to improving the therapeutic index of IL-2-based therapy is to use variants of IL-2 that are selective for Treg cells relative to other immune cells. IL-2 receptors are expressed on a variety of different immune cell types, including T cells, NK eosinophils, and monocytes, and this broad expression pattern likely contributes to its pleiotropic effect on the immune system and high systemic toxicity. The IL-2 receptor exists in three forms: (1) the low affinity receptor, IL2RA, which does not signal; (2) the intermediate affinity receptor (IL2Rβγ), composed of IL2RB and IL2RG, which is broadly expressed on conventional T cells (Tcons), NK cells, eosinophils, and monocytes; and (3) the high affinity receptor (IL2Rαβγ), composed of IL2RA, IL2RB, and IL2RG, which is expressed transiently on activated T cells and constitutively on Treg cells, IL-2 variants have been developed that are selective for IL2Rαβγ relative to IL2Rβγ (Shanafelt, A. B., et al., 2000, Nat Biotechnol. 18: 1197-202; Cassell, D. J., et. al., 2002, Curr Pharm Des., 8:2171-83). These variants have amino acid substitutions which reduce their affinity for IL2RB. Because IL-2 has undetectable affinity for IL2RG, these variants consequently have reduced affinity for the IL2Rβγ receptor complex and reduced ability to activate IL2Rβγ-expressing cells, but retain the ability to bind IL2RA and the ability to bind and activate the IL2Rαβγ receptor complex. One of these variants, IL2/N88R (Bay 50-4798), was clinically tested as a low-toxicity version of IL-2 as an immune system stimulator, based on the hypothesis that IL2Rβγ-expressing NK cells are a major contributor to toxicity. Bay 50-4798 was shown to selectively stimulate the proliferation of activated T cells relative to NK cells, and was evaluated in phase clinical trials in cancer patients (Margolin, K., et. al., 2007, Clin Cancer Res., 13:3312-9) and HIV patients (Davey, R. T., et. al., 2008, J Interferon Cytokine Res., 28:89-100). These trials showed that Bay 50-4798 was considerably safer and more tolerable than Proleukin, and also showed that it increased the levels of CD4+ T cells and CD4+CD25+ T cells in patients. However, the increase in CD4+ T cells and CD4+CD25+T cells were not indicative of an increase in Treg cells, because identification of Tregs requires additional markers in addition to CD4 and CD25, and because Treg cells are a minor fraction of CD4+CD25+ cells. Subsequent to these trials, research in the field more fully established the identity of Treg cells and demonstrated that Treg cells selectively express IL2Rαβγ (reviewed in Malek, T. R., et al., 2010, immunity, 33:153-65). Based on this new research, it can now be understood that IL2Rαβγ selective agonists should be selective for Treg cells.

A second approach to improving the therapeutic index of an IL-2 based therapy is to optimize the pharmacokinetics of the molecule to maximally stimulate Treg cells. Early studies of IL-2 action demonstrated that IL-2 stimulation of human T cell proliferation in vitro required a minimum of 5-6 hours exposure to effective concentrations of IL-2 (Cantrell, D. A., et, al., 1984, Science, 224: 1312-1316). When administered to human patients, IL-2 has a very short plasma half-life of 85 minutes for intravenous administration and 33 hours subcutaneous administration (Kirchner, G. I., et al., 1998, Br J Clin Pharmacol, 46:5-10). Because of its short half-life, maintaining circulating IL-2 at or above the level necessary to stimulate T cell proliferation for the necessary duration necessitates high doses that result in peak IL-2 levels significantly above the EC50 for Treg cells or will require frequent administration (FIG. 1). These high IL-2 peak levels can activate IL2Rβγ receptors and have other unintended or adverse effects. An IL-2 analog with a longer circulating half-life than IL-2 can achieve a target drug concentration for a specified period of time at a lower dose than IL-2, and with lower peak levels. Such an IL-2 analog will therefore require either lower doses or less frequent administration than IL-2 to effectively stimulate Treg cells. Indeed, in cynomolgus monkeys dosed with an IgG-IL2 fusion protein with a circulating half-life of 14 hours stimulated a much more robust increase in Tregs compared to an equimolar dose of IL-2 (Bell, et al., 2015, J Autoimmun. 56:66-80). Less frequent subcutaneous administration of an IL-2 drug will also be more tolerable for patients. A therapeutic with these characteristics will translate clinically into improved pharmacological efficacy, reduced toxicity, and improved patient compliance with therapy.

One approach to extending the half-life of therapeutic proteins is to fuse the therapeutically active portion of the molecule to another protein, such as the Fc region of IgG, to increase the circulating half-life: Fusion of therapeutic proteins with IgG Fc accomplishes this by increasing the hydrodynamic radius of the protein, thus reducing renal clearance, and through Neonatal Fc. Receptor (FcRn)-mediated recycling of the fusion protein, thus prolonging the circulating half-life. The fusion of therapeutic proteins to albumin (Sleep, D., et. al., 2013, Biochem Biophys Acta., 1830:5526-34) and nonimmunogenic amino acid polymer proteins (Schlapschy, M., et. al., 2007, Protein Eng Des Sel. 20:273-84; Schellenberger, V., et al., 2009, Nat Biotechnol. 27:1186-90) have also been employed to increase circulating half-life. However, construction of such fusion proteins in a manner that ensures robust biological activity of the IL2 Selective Agonist fusion partner can be unpredictable, especially in the case of an IL-2 Selective Agonist, which is a small protein that is defective in binding to one of the receptor subunits and that must assemble a complex of three receptor subunits in order to activate the receptor (Wang, X., et al., 2005, Science 310:1159-63).

Other researchers have created various IL-2 fusion proteins, using wild-type IL-2 or IL-2 with a (125S substitution to promote stability. Morrison and colleagues (Penichet, M. L., et. al., 1997, Hum Antibodies. 8:106-18) created a fusion protein with IgG fused to wild-type IL-2 to both increase the circulating half-life of IL-2 and to target IL-2 to specific antigens for the purpose of potentiating the immune response to the antigen. This fusion protein consisted of an intact antibody molecule, composed of heavy (H) and light (L) chains, wherein the N-terminal H chain moiety was fused to a C-terminal IL-2 protein moiety. This IgG-IL-2 fusion protein possessed Fc effector functions. Key effector functions of IgG Fc proteins are Complement-dependent cytotoxicity (CDC) and antibody-dependent cellular cytotoxicity (ADCC). The IgG-IL-2 fusion protein was highly active in an IL-2 bioassay and was shown to possess CDC activity. Thus, Penichet et. al. taught the use of antibody-IL2 fusion proteins to target IL-2 activity to antigens recognized by the antibody, for the purpose of potentiating humoral and cell-mediated immune responses to the antigen. In a similar manner, Gillies and colleagues have constructed a number of IgG-IL-2 fusion proteins for cancer immunotherapy, utilizing the antibody portion of the fusion protein to target tumor antigens, and the IL-2 portion to stimulate the immune response to tumor cells (reviewed in Sondel, P. M., et. al., 2012, Antibodies, 1:149-71). These teachings are quite distinct from the present inventive technology, wherein an IL-2 selective agonist, which promotes the growth and activity of immunosuppressive Treg cells, is fused with an effector function-deficient Fc protein moiety for the purpose increasing systemic exposure.

Strom and his colleagues have constructed fusion proteins with IL-2 fused to the N terminus of an Fc protein for the purpose of eliminating activating T cells expressing the high-affinity IL-2 receptor (Meng, X. X., et al., 1999, J Immunol. 1999, 163:4041-8). This fusion protein was shown to inhibit the development of autoimmune diabetes in a T cell transfer mouse model of T1D. The IL2-Fc fusion protein was shown to inhibit the function of disease-promoting T cells from T1D-susceptible female NOD mice when transplanted into less disease-susceptible male NOD mice. They also demonstrated that the IL-2-Fc fusion protein could kill cells expressing the high-affinity IL-2 receptor in vitro. These investigators further compared IL2-Fc fusion proteins constructed from an Fc derived from an effector function-competent IgG2b Fc and a mutated effector function-deficient IgG2b Fc. Only the IL2-Fc fusion protein containing the effector function-competent Fc was efficacious in preventing disease onset. Thus, these investigators teach that an IL2-Fc fusion protein with effector functions can eliminate disease-causing activated T cells, and that Fc effector functions are necessary for its therapeutic activity. These teachings are quite distinct from the present inventive technology, wherein an IL-2 selective agonist, which promotes the growth and activity of immunosuppressive Treg cells, is fused with an effector function-deficient Fc protein moiety for the purpose increasing systemic exposure and optimizing Treg expansion. Other work from Strom and colleagues teaches the use of a IL2-Fc fusion protein in promoting transplant tolerance (Zheng, X. X., et al., 2003, Immunity, 19:503-14). In this work, an IL2-Fc fusion protein is used in a "triple therapy" in which it is combined with an IL 15-Fc receptor antagonist and rapamycin. Again, these investigators teach that the IL2-Fc fusion protein must have Fc effector functions to be efficacious, and farther teach that this IL-2-Fc fusion protein must be combined with two other molecules in order to be efficacious.

This invention provides for a novel therapeutic agent, an IL2 Selective Agonist Fc fusion protein with a peptide linker of from 6-30 amino acids. This configuration combines the high cellular selectivity of a IL2. Selective Agonist for Treg cells with a long circulating half-life. In the course of developing this molecule, there were surprising and unexpected findings that revealed structural elements and design features of the protein that are essential for bioactivity, and that led to the discovery of several novel proteins that fulfill the desired therapeutic characteristics.

BRIEF SUMMARY OF THE INVENTION

This invention provides for a fusion protein between an IL2αβγ Selective Agonist protein (IL2 Selective Agonist) and a IgG Fc protein where the IL2 agonist and the Fc protein are separated by a linker of 17 Å to 105 Å and configured so the IL2 agonist is at the N terminus of the molecule and the Fc protein is at the C terminus. The IL2 Selective Agonist moiety provides a therapeutic activity by selectively activating the IL2αβγ form of the receptor, thus selectively stimulating Tregs. The Fc moiety provides a prolonged circulating half-life compared to the circulating half-fife of IL-2 or an IL2 Selective Agonist protein. The Fc moiety increases circulating half-life by increasing the molecular size of the fusion protein to greater than 60,000 daltons, which is the approximate cutoff for glomerular filtration of macromolecules by the kidney, and by recycling the fusion protein through the Neonatal Fc Receptor (FcRn) protein, the receptor that binds and recycles IgG, thus prolonging its circulating half-life. The Fc moiety will also be deficient in Fc effector functions, such as Complement-Dependent Cytotoxicity (CDC) and Antibody-Dependent Cellular Cytotoxicity (ADCC), enabling the fusion protein to selectively activate Tregs to potentiate Treg function and to expand Treg numbers. The two protein moieties are fused in a manner that maintains robust bioactivity of the IL2 Selective Agonist moiety and enables the Fc moiety to promote a prolonged circulating half-life and thus efficiently potentiate Tregs function and numbers. This potentiation of Tregs will suppress over-exuberant autoimmune or inflammatory responses, and will be of benefit in treating autoimmune and inflammatory diseases. The proteins of this invention may be monomeric or dimeric forming dimers through cysteine residues in the Fc moieties or domains.

More specifically, this invention provides for a fusion protein, comprising: a N-terminal human IL-2 variant protein moiety, and a C-terminal IgG Fc protein moiety, wherein said IL-2 fusion protein has the ability to selectively activate the high affinity IL-2 receptor and thus selectively activate human regulatory T cells. The variants of IL-2 include those with substitutions selected from the group consisting of: N88R, N88G, D20H, Q126L, and Q126F relative to human IL2 protein. SEQ ID NO:1 is variant IL-2/N88R, with the numbering corresponding to wt IL2. In addition, the IL-2 variant protein optionally comprises human IL-2 with the substitution C125S. It is preferred that the proteins of this invention are fused wherein both the IL-2 variant protein and the IgG Fc protein have an N terminus and a C-terminus and said human IL-2 variant protein is fused at its C-terminus to the N-terminus of the IgG Fc protein. It is further disclosed that the activity of the IL-2 variant domain is greatly enhanced when a linker peptide positioned between the IL-2 variant protein and the IgG Fc protein moieties. The IgG Fc protein moiety or domain will optionally be deficient in Fc effector functions or contain one or more amino acid substitutions that reduce the effector functions of the Fc portion of the fusion protein.

An example of this invention is a protein, comprising: a IL-2 variant protein having amino acid substitutions N88R and C125S relative to human IL-2 (SEQ ID NO:1-N88R), a linker peptide as set forth in SEQ ID NO: 15, and a human IgG1 Fc protein having the substitution N297A as set forth in SEQ ID NO:2, wherein said fusion protein has the ability to selectively activate the high affinity IL-2 receptor and thus selectively activate human regulatory T cells. Alternative proteins of this invention include: a IL-2 variant protein having amino acid substitutions N88R and C125S relative to human IL-2 (SEQ ID NO:1-N88R), a linker peptide as set forth in SEQ ID NO: 15, and a human IgG2 Fc protein as set forth in SEQ ID NO:3.

A more specific embodiment of this invention is a dimeric protein, comprising two identical chains, where each chain comprises a N-terminal human IL-2 variant protein moiety and a C-terminal IgG Fc protein moiety wherein: the N-terminal human IL-2 variant protein moiety has a N-terminus and a C-terminus varies from the human IL-2 wildtype as in SEQ ID NO: 1 by at least one of the substitutions selected from the group consisting of: N88R, N88G, D20H, Q126L, and Q126F, has at least a 90 or 95 or 97% sequence identity to Sequence ID No. 1; and, has the ability to activate Treg cells by binding to a IL2Rαβγ on those cells; the N-terminal human IL-2 variant protein is joined at its C-terminal to a N-terminus of an amino acid linker of between 6 to 20 or 6 to 30 amino add residues where said linker also has a C-terminus; and, the C-terminus of the amino acid linker is joined to the N terminus of IgG Fc protein moiety having 90 or 95 or 97% sequence identity to for example SEQ ID NO: 3 (IgG2) or SEQ ID No. 2 (IgG1N297A) and containing cysteine residues; and where the two chains are linked to each other through the cysteine residues that form the interchain disulfide bonds of the IgG Fc protein moiety. The dimers of this invention may be further substituted at C125S of the IL-2 moiety. The proteins of this invention preferably include amino acid linkers consisting a group of glycine residues, serine residues, and a mix of glycine and serine residues. The linkers may comprise a mix of between 12 and 17 serine and glycine residues preferably with a ratio of glycine residues to serine residues in a range of 3:1-5:1, e.g, a 4:1 ratio.

This invention further provides for the compositions above in a pharmaceutical composition comprising a pharmaceutically acceptable carrier.

This invention further provides for nucleic acids encoding the proteins described herein. The nucleic acids are preferably operably linked to expression cassettes that can be either designed for recombination with a host cell genome or introduced on an independently replicating plasmid or extra-chromosomal nucleic acid.

This invention further provides for methods of selectively activating human regulatory T cells in a patient in need thereof, the method comprising administering a pharmaceutical composition comprising the compositions described administered at therapeutically effective doses until human regulatory T cell concentrations reach desired levels.

A method of measuring the numbers of Treg cells in a human blood sample by contacting human blood cells with the fusion protein of claim 1 at a concentration of between 1 nM and 0.01 nM, and then detecting cells that bind to the protein by flow cytometry.

BRIEF DESCRIPTION OF THE DRAWINGS

FIG. 3A. N88RL9AG1 stimulates only CD25$^{high}$ cells with high selectivity, while IL-2 massively stimulates both CD25$^{-/low}$ and CD25$^{high}$ cells down to picomolar concentrations. FIG. 3B. D20HL0G2 has no pSTAT5 stimulating activity. No pSTAT5 activation was observed in two independent experiments. FIG. 3C. Control showing that D20H/IL2 stimulates pSTAT5 in CD25$^{high}$ cells while D20HL0G2 does not. Plots are displayed in the pseudocolor mode. Both proteins were tested at a concentration of $10^{-8}$ M.

FIG. 5A. Protein yields of N88R/IL2-Fc fusion proteins increase with increasing peptide linker length. FIG. 5B. Yields of wt IL2-Fc fusion proteins are only slightly enhanced with a 15 residue peptide linker. Higher yields of D20H/IL2-Fc fusion proteins were obtained in the X-Fc rather than the Fc-X configuration.

(FIG. 6A) pSTAT5 signals in CD25$^{high}$ CD4+ T cells (Tregs) increase with increasing peptide linker length, (FIG. 6B) No significant pSTAT5 signal with any of N88R/IL2-Fc proteins was observed in CD25$^{-/low}$ cells. The pSTAT5 signal of the $10^{-8}$ M IL-2 internal control is indicated in both panels by the black triangle.

DETAILED DESCRIPTION OF THE INVENTION

Introduction

Figure 1:
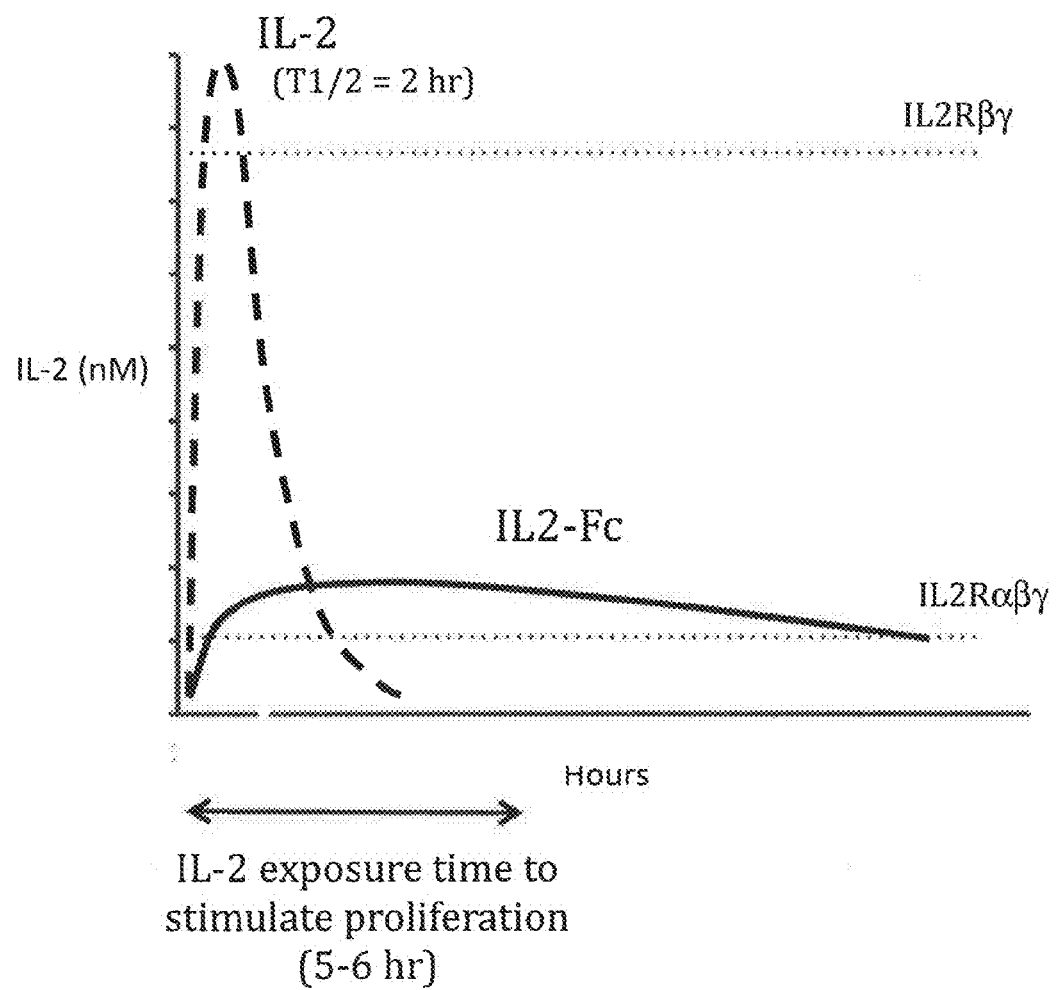
FIG. 1 is a diagrammatic illustration of the relationship between circulating half-life, peak drug level, the biological effective concentration, and the duration necessary to stimulate Treg cell proliferation after a single dose of IL-2 or an IL2-Fc fusion protein with increased half-life. The dashed line represents the blood level over time of IL-2 following a subcutaneous injection, and the solid line represents the blood level over time of an IL2-Fc fusion protein. The horizontal dotted lines indicate the concentrations (EC50 values) necessary to activate cells expressing IL2Rαβγ and IL2Rβγ, respectively) are indicated. The double-headed arrow indicates the duration of exposure (5-6 hr) to IL-2 at the EC50 necessary to stimulate cell proliferation.

This invention is a novel therapeutic fusion protein that comprises three key protein elements: (1) an engineered IL-2 cytokine that has been modified to be highly selective for Treg cells, (2) an effector function deficient Fc protein that will increase the circulating half-life of the protein, and (3) a peptide linker between the two moieties that is necessary for high biological activity of the fusion protein. The fusion proteins are configured such that the IL-2 domain is attached to the N-terminus of a linker peptide through the C-terminus of the IL-2 domain. The Fc domain being attached through its N-terminus to the C-terminus of the linker. In prior studies with and without short peptide linkers, it was reported that the n-IL-2:c-Fc fused proteins lacked significant bioactivity. This lead to a focus on reverse configurations n-Fc:c-IL-2 where the Fc regions were attached N-terminus of the linker and the IL-2 domains formed the carboxy terminus of the fusion protein.

An Fc fusion protein with a bioactive fusion partner domain on the N-terminus of the Fc is a preferred configuration, because the bioactive domain replaces the Fab portion of IgG. An Fc fusion protein with a bioactive fusion partner domain on the C-terminus of the Fc is a less preferred configuration because the C-terminus of IgG Fc potentially impaired in its ability to bind to other molecules, such as the Fc receptor FcRn, which is required for the long circulating half-life of Fc proteins. IL2 fusion proteins fused to the C-terminus of Fc have been reported to have much shorter circulating half-lives than would be expected for an Fc fusion protein, suggesting that the function or the stability of the Fc is impaired. Accordingly, this invention with its long peptide linker that is necessary for IL-2 bioactivity represents a significant and unanticipated advance that went against teachings in the prior art of IL-2 fusion proteins. The molecules defined by this invention will enable the safe and effective treatment of autoimmune diseases by the novel mechanism of stimulating the production of a small subpopulation of T cells that suppress autoimmune and inflammatory pathology. This paradigm-breaking therapeutic is expected to treat a number of different autoimmune diseases.

Definitions

"At least a percent (eg. 90 or 95 or 97%) sequence identify to Sequence ID No. 1" as used herein refers to the extent to which the sequence of two or more nucleic acids or polypeptides is the same. The percent identity between a sequence of interest and a second sequence over a Window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. ScL USA 87:22264-2268, 1990) modified as in Karlin and Altschul, Proc. Natl. Acad. ScL USA 90:5873-5877, 1993 is incorporated into the NBLAST and XBLAST programs of Altschul et at (Altschul, et at, J. Mol. Biol. 215:403-410, 1990). To obtain gapped alignments for comparison purposes, Gapped BLAST is utilized as described in Altschul et at (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL world-wide web address of: "ncbi.nlm.nih.gov" for these programs. In a specific embodiment, percent identity is calculated using BLAST2 with default parameters as provided by the NCBI.

"N-terminus" refers to the end of a peptide or polypeptide that bears an amino group in contrast to the carboxyl end hearing a carboxyl acid group.

"C-terminus" refers to the end of a peptide or polypeptide that bears a carboxcylic acid group in contrast to the amino terminus bearing an amino group.

"C-terminal IgG Fc protein moiety" refers to a portion of a fusion protein that derives from two identical protein fragments, each having a hinge region, a second constant domain, and a third constant domains of the IgG molecule's two heavy chains, and consisting of the carboxy-terminal heavy chains disulphide bonded to each other through the hinge region. It is functionally defined as that part of the IgG molecule that interacts with the complement protein C1q and the IgG-Fc receptors (FcγR), mediating Complement-dependent cytotoxicity (CDC) and antibody-dependent cellular cytotoxicity (ADCC) effector functions. The sequence can be modified to decrease effector functions, to increase circulating half-life, and to eliminate glycoslylation sites.

IL2 Variants

IL-2 variant proteins of this invention are IL-2αβγ Selective Agonists. Functionally they selectively activate the IL2Rαβγ receptor complex relative to the IL2Rβγ receptor complex. It is derived from a wild type IL-2 protein structurally defined as having at least a 95% sequence identity to the wild type IL-2 of Sequence ID No. 1 and functionally defined by the ability to preferentially activate Treg cells. The protein can also be functionally defined by its ability to selectively activate IL-2 receptor signaling in Tregs, as measured by the levels of phosphorylated STAT5 protein in Treg cells compared to CD4+ CD25−/low T cells or NK cells, or by the selective activation of Phytohemagglutinin-stimulated T cells versus NK cells.

"N-terminal human IL-2 variant protein moiety" refers to a N-terminal domain of a fusion protein that is derived from a wild type IL-2 protein structurally and functionally defines above.

"C-terminus" refers to the end of a peptide or polypeptide that bears a carboxylic acid group in contrast to the amino terminus bearing an amino group.

Tregs

"Tregs" or "Treg cells" refer to Regulatory T cells. Regulatory T cells are a class of T cells that suppress the activity of other immune cells, and are defined using flow cytometry by the cell marker phenotype CD4+CD25+FOXP3+. Because FOXP3 is an intracellular protein and requires cell fixation and permeabilization for staining, the cell surface phenotype CD4−CD25+CD127− can be used for defining live Tregs. Tregs also include various Treg subclasses, such as tTregs (thymus-derived) and pTregs (peripherally-derived, differentiated from naïve T cells in the periphery). All Tregs express the IL2Rαβγ receptor, do not produce their own IL-2 and are dependent on IL-2 for growth, and someone skilled in the art will recognize that both classes will be selectively activated by a IL2Rαβγ selective agonist.

Peptide Linkers

"Peptide linker" is defined as an amino acid sequence located between the two proteins comprising a fusion protein, such that the linker peptide sequence is not derived from either partner protein. Peptide linkers are incorporated into fusion proteins as spacers in order to promote proper protein folding and stability of the component protein moieties, to improve protein expression, or to enable better bioactivity of the two fusion partners (Chen, et al., 2013, Adv Drug Deliv Rev. 65(10):1357-69). Peptide linkers can be divided into the categories of unstructured flexible peptides or rigid structured peptides.

Fc Fusion Proteins

An "Fc fusion protein" is a protein made by recombinant DNA technology in which the translational reading frame of the Fc domain of a mammalian IgG protein is fused to that of another protein ("Fc fusion partner") to produce a novel single recombinant polypeptide. Fc fusion proteins are typically produced as disulfide-linked dimers, joined together by disulfide bonds located in the hinge region.

Functional Activation

"Bioactivity" refers to the measurement of biological activity in a quantitative cell-based in vitro assay.

"Functional activation of Treg cells" is defined an IL-2-mediated response in Tregs. Assay readouts for functional activation of Treg cells includes stimulation of pSTAT5, Treg cell proliferation, and stimulation of the levels of Treg effector proteins.

Design and Construction

There are multiple options for the design and construction of an Fc fusion protein, and the choices among these design options are presented below to permit the generation of a molecule with the desired biological activity and pharmaceutical characteristics. Key design options are: (1) the nature of the IL2 Selective Agonist, (2) the choice of the Fc protein moiety, (3) the configuration of fusion partners in the fusion protein, and (4) the amino acid sequence at the junction between the Fc and the fusion partner protein.

General Methods

In general, preparation of the fusion proteins of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the fusion molecules can be isolated and purified using chaotropic agents and well known electrophoretic, centrifugation and chromatographic methods. See generally, Sambrook et al., Molecular Cloning: A Laboratory Manual (2nd ed. (1989); and Ausubel et al., Current Protocols in Molecular Biology, John Wiley & Sons, New York (1989) for disclosure relating to these methods.

The genes encoding the fusion proteins of this invention involve restriction enzyme digestion and ligation as the basic steps employed to yield DNA encoding the desired fusions. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of E. coli. Numerous cloning vectors suitable for construction of the expression construct are known in the art (lambda.ZAP and pBLUESCRIPT SK-1 Stratagene, LaJolla, Calif., pET, Novagen Inc., Madison, Wis.—cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

Site-directed mutagenesis is typically used to introduce specific mutations into the genes encoding the fusion proteins of this invention by methods known in the art. See, for example, U.S. Patent Application Publication 2004/0171154; Storici et al., 2001, Nature Biotechnology 19: 773-776, Kren et al., 1998, Nat. Med. 4: 285-290; and Calissano and Macino, 1996, Fungal Genet. Newslett. 43: 15-16. Any site-directed mutagenesis procedure can be used in the present invention. There are many commercial kits available that can be used to prepare the variants of this invention.

Various promoters (transcriptional initiation regulatory region) may be used according to the invention. The selection of the appropriate promoter is dependent upon the proposed expression host. Promoters from heterologous sources may be used as long as they are functional in the chosen host.

Various signal sequences may be used to facilitate expression of the proteins described herein. Signal sequence are selected or designed for efficient secretion and processing in the expression host may also be used. A signal sequence which is homologous to the TCR coding sequence or the mouse IL-2 coding sequence may be used for mammalian cells. Other suitable signal sequence/host cell pairs include the B. subtilis sacB signal sequence for secretion in B. subtilis, and the Saccharomyces cerevisiae α-mating factor or P. pastoris acid phosphatase pho1 signal sequences for P. pastoris secretion. The signal sequence may be joined directly through the sequence encoding the signal peptidase cleavage site to the protein coding sequence, or through a short nucleotide bridge.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400 fold in plant cells. The expression construct should also include the appropriate translational initiation sequences. Modification of the expression construct to include a Kozak consensus sequence for proper translational initiation may increase the level of translation by 10 fold.

The expression cassettes are joined to appropriate vectors compatible with the host that is being employed. The vector must be able to accommodate the DNA sequence coding for the fusion proteins to be expressed. Suitable host cells include eukaryotic and prokaryotic cells, preferably those cells that can be easily transformed and exhibit rapid growth in culture medium. Specifically preferred hosts cells include prokaryotes such as E. coli, Bacillus subtillus, etc. and eukaryotes such as animal cells and yeast strains, e.g., S. cerevisiae. Mammalian cells are generally preferred, particularly HEK, J558, NSO, SP2-O or CHO. Other suitable hosts include, e.g., insect cells such as Sf9. Conventional culturing conditions are employed. See Sambrook, supra. Stable transformed or transfected cell lines can then be selected. In vitro transcription-translation systems can also be employed as an expression system.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Alternatively, one can use synthetic gene construction for all or part of the construction of the proteins described herein. This entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et al., Nature 432:1050-1054) and similar technologies wherein olgionucleotides are synthesized and assembled upon photo-programmable microfluidic chips.

The fusion proteins of this invention are isolated from harvested host cells or from the culture medium. Standard protein purification techniques are used to isolate the proteins of interest from the medium or from the harvested cells. In particular, the purification techniques can be used to express and purify a desired fusion protein on a large-scale (i.e. in at least milligram quantities) from a variety of approaches including roller bottles, spinner flasks, tissue culture plates, bioreactor, or a fermentor.

The IL2 Selective Agonist Moiety

IL-2 with the substitution N88R is an exemplary case of an IL2 Selective Agonist for the IL2Rαβγ receptor (Shanafelt, A. B., et al., 2000, Nat Biotechnol. 18:1197-202). IL2/N88R is deficient in binding to the IL2Rβ receptor subunit and the IL2Rβγ receptor complex, but is able to bind to the IL2Rαβγ receptor complex and stimulate the proliferation of IL2Rαβγ-expressing PHA-activated T cells as effectively as wt IL-2, while exhibiting a 3,000 fold reduced ability to stimulate the proliferation of IL2Rβγ-expressing NK cells, Other IL2Rαβγ selective agonists with similar activity profiles include IL-2 with the substitutions N88G, and D20H, and other IL2 variants with the substitutions Q126L and Q126F (contact residues with the IL2RG subunit) also possess IL2Rαβγ-selective agonist activity (Cassell, D. J., et. al., 2002. Curr Pharm Des., 8:2171-83). A practitioner skilled in the art would recognize that any of these IL2 Selective Agonist molecules can be substituted for the IL2/N88R moiety with the expectation that an Fc fusion protein will have similar activity. All of the aforementioned mutations can be made on the background of wt IL-2, or wt IL-2 with the substitution C125S, which is a substitution that promotes IL-2 stability by eliminating an unpaired cysteine residue. This invention can also be used with other mutations or truncations that improve production or stability without significantly impacting IL-2 receptor activating activity.

The variants of this invention optionally include conservatively substituted variants that apply to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed base and/or deoxyinosine residues (Batzer et al., Nucleic Acid Res, 19:5081 (1991); Ohtsuka et al., J. Biol. Chem. 260:2605-2608 (1985); Rossolini et al., Mol. Cell. Probes 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With regard to conservative substitution of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine Leucine (L), Valine (V); and
8) Phenylalanine (F), Tyrosine (Y), Tryptophan (W).

The PC Protein Moiety

A key design choice is the nature of the Fc protein moiety. The main therapeutic applications of Fc fusion proteins are (1) endowing the fusion partner protein with immunoglobulin Fc effector functions; or (2) increasing the circulating half-life of the fusion partner protein (Czajkowsky, et al., 2012, EMBO Mol Med. 4:1015-28). The primary effector functions of IgG proteins are Complement-Dependent Cytotoxicity (CDC) and Antibody-Dependent Cellular Cytotoxicity (ADCC), functions mediated by Fc binding to complement protein C1q and to IgG-Fc receptors (FcγR), respectively. These effector functions are important when the therapeutic protein is used to direct or enhance the immune response to a particular antigen target or cell. The fusion protein of this invention is designed solely to increase the circulating half-life of the IL2 Selective Agonist moiety, and effector functions are not needed and can even be toxic, and thus expressly not desired. For instance, an IL2 Selective Agonist-Fc fusion protein with an effector function-competent Fc can potentially kill the Treg cells that the fusion protein of this invention is seeking to activate and expand, exactly the opposite of the therapeutic goal for autoimmune diseases. There are four human IgG subclasses which differ in effector functions (CDC, ADCC), circulating half-life, and stability (Salfeld, J. G., 2007, Nature Biotechnology 25:1369-72). IgG1 possesses Fc effector functions, is the most abundant IgG subclass, and is the most commonly used subclass in US FDA-approved therapeutic proteins. IgG2 is deficient in Fc effector functions, but is subject to dimerization with other IgG2 molecules, and is also subject to instability due to scrambling of disulfide bonds in the hinge region. IgG3 possesses Fc effector functions, and has an extremely long, rigid hinge region, IgG4 is deficient in Fc effector functions, has a shorter circulating half-life than the other subclasses, and the IgG4 dimer is biochemically unstable due to only a single disulfide bond in the hinge region leading to the exchange of H chains between different IgG4 molecules. A skilled artisan would recognize that Fc protein moieties from IgG2 and IgG4 do not possess effector functions and can be used in this invention. The skilled artisan would also recognize that Fc sequence modifications have been described in the art that such that the hinge region of IgG2 Fc can be modified to prevent aggregation, or that the hinge region of IgG4 Fc can be modified to stabilize dimers. Alternatively, effector function-deficient variants of IgG1 have been generated. One such variant has an amino acid substitution at position N297, the location of an N-linked glycosylation site. Substitution of this asparagine residue removes the glycosylation site and significantly reduces ADCC and CDC activity (Tao, M. H., et al., 1989, J Immunol. 143:2595-2601). This variant is used as an exemplary case in the invention herein. Another effector function deficient IgG1 variant is IgG1(L234F/L235E/P331S/) (Oganesyan, et al., 2008, Acta Crystallogr D Biol Crystallogr, 64; 700-4), which mutates amino acids in the C1q and FcγR binding sites, and one skilled in the art would consider using these or similar Fc variants to generate effector-deficient and stable IL2SA-Fc fusion proteins. A skilled artisan would also recognize that forms of Fc protein moieties engineered to be stable monomers rather than dimers (Dumont, J. A., et., al., 2006, BioDrugs 20:151-60; Liu Z, et al., 3 Biol Chem. 2015 20; 290:7535-62) can also be combined with the IL-2 selective agonist of this invention. In addition, a skilled artisan would recognize that a functionally monomeric heterodimer composed of an IL-2-Fc H chain polypeptide combined with an Fc H chain polypeptide and assembled using bispecific antibody technology (Zhu Z, et al., 1997 Protein Sci. 6:781-8) can also be combined with the IL-2 Selective Agonist of this invention. Some IL-2 Fc fusion proteins have been made with intact IgG antibody molecules, either with (Penichet, M. L., et., al., 1997, Hum Antibodies. 8:106-18) or without (Bell, et al., 2015, 3 Autoimmun, 56:66-80) antigen specificity in the IgG moiety. In addition, a skilled artisan will recognize that Fc variants that lack some or all of the hinge region can be used with this invention.

Figure 2:
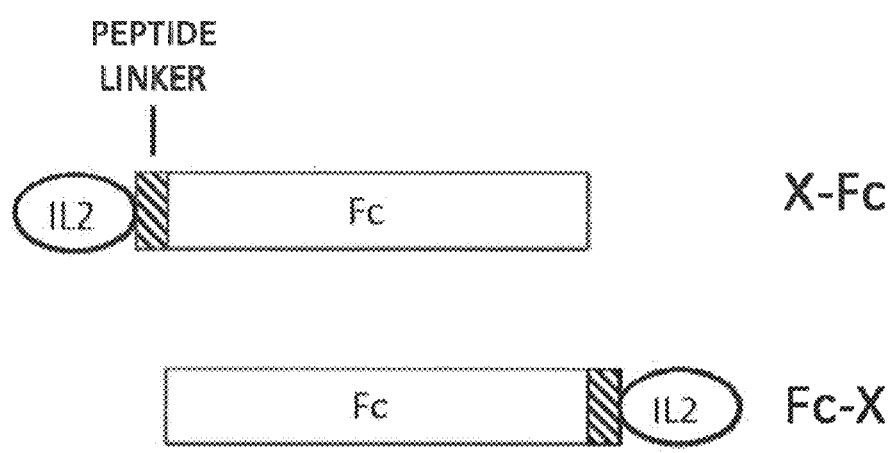
FIG. 2 shows the design configurations for Fc fusion proteins. The fusion partner (X), can be fused at the N terminus (X-Fc) or the C-terminus (Fc-X) of the Fc protein. Linker peptides can be inserted between X and the Fc.

Fc fusion proteins can be made in two configurations, indicated here as X-Fc and Fc-X, where X, the fusion partner protein, is at the N-terminus and Fc is at the C-terminus, and Fc-X, where the Fc is at the N-terminus, and fusion partner protein is at the C-terminus (FIG. 2). There are examples in the literature showing that different fusion partners can have distinct preferences for N- or C-terminal Fc fusions. For instance, FGF21 has been shown to have a strong preference for the Fc-X configuration. Fc-FGF21 has receptor-activating bioactivity essentially the same as FGF21 itself, while FGF21-Fc has 1000-fold reduced bioactivity (Hecht, et al., 2012, PLoS One. 7(11):e49345). A number of IL-2 Fc fusion proteins have been made for various applications, and these have been reported to have good IL-2 bioactivity when directly fused to Fc in both the Fc-X (Gillies, et al., 1992, Proc Natl Acad Sci, 89:1428-32; Bell, et al., 2015, J Autoimmun. 56; 66-80) and X-Fc (Zheng, X. X., et al., 1999, J Immunol, 163:4041-8) configurations. Gavin, et al. (US 20140286898 A1) describes Fc fusion proteins containing IL-2 and certain IL-2 variants in the in the Fc-X configuration that have bioactivity similar to that of the free IL-2 cytokine, hut in contrast to the results of Meng et al. (Zheng, X. X., et al, 1999, J Immunol. 1999, 163:4041-8) found that IL-2 variant fusion proteins in the X-Fc configuration have reduced or no bioactivity. Thus, Gavin, et al. generally teaches away from N-terminal IL-2 Fc fusion proteins. Another factor that influences the choice of fusion protein configuration is the impact on circulating half-life. A recurring finding in the literature is that IL-2 fusion proteins in the Fc-X configuration have relatively low circulating half-lives, much less than the 21 day half-life of human IgG1 in humans or the half-lives of current FDA-approved Fc fusion proteins (TABLE I). IgG-IL2 fusion proteins in the Fc-X configuration have been reported to have relatively short circulating half-lives on the order of hours in mice (Gillies S. D., 2002 Clin Cancer Res., 8:210-6; Gillies, S. D., US 2007/0036752 A2; Bell C. J., 2015 J Autoimmun. 56:66-80) and on the order of 3.3 hours (Ribas A., J 2009 Transl Med. 7:68) and 3.7 hours (King D. M., 2004 J Clin Oncol., 22:4463-73) in humans, and Fc-IL2 fusion proteins have been reported to have circulating half-lives of 12.5 hours in mice (Zhu F. F., Cancer Cell. 2015, 13; 27(4):489-501). Proteolysis between the C-terminus of the Fc moiety and the IL-2 moiety contributes to the short circulating half-lives (Gillies S. D., 2002 Clin Cancer Res., 8:210-6; Zhu E. F., 2015 Cancer Cell, 27:489-501). Because of these relatively short half-lives, we have focused on IL2 Selective Agonist Fc fusion proteins in the X-Fc configuration. The findings in this work indicate that an IL2-Fc fusion protein containing the IgG1(N297A) substitution has high bioactivity and is an especially preferred species of this invention. A variant of the IgG1 Fc fusion protein that eliminates the O-linked carbohydrate is also an especially preferred species, since it is highly bioactive and provides advantages for the manufacturing of a pure and homogeneous drug product. The findings in this patent further indicate that IL2-Fc fusion proteins with the effector function-deficient IgG1 variant and the IgG4 Fc, while slightly less active, are also preferred species. Fusion with IgG2 and Serum Albumin (HSA) have lower bioactivity, and are less preferred species, although they may be suitable for therapeutic use if they possess other positive attributes.

Linker

The amino acid sequence at the junction between the Fc and the fusion partner protein can be either (1) a direct fusion of the two protein sequences or (2) a fusion with an intervening linker peptide. Of the 10 Fc fusion proteins that are presently approved by the US FDA for clinical use (TABLE 1), 8 are direct fusions of the fusion partner protein with Fc, while 2 possess linker peptides, so many Fc fusion proteins can be functional without linker peptides. Linker peptides are included as spacers between the two protein moieties. Linker peptides can promote proper protein folding and stability of the component protein moieties, improve protein expression, and enable better bioactivity of the component protein moieties (Chen, et al., 2013, Adv Drug Deliv Rev, 65:1357-69). Peptide linkers used in many fusion proteins are designed to be unstructured flexible peptides. A study of the length, sequence, and conformation of linkers peptides between independent structural domains in natural proteins has provided a theoretical basis for the design of flexible peptide linkers (Argos, 1990J Mol Biol. 211:943-58). Argos provided the guidance that long flexible linker peptides be composed of small nonpolar residues like Glycine and small polar resides like Serine and Threonine, with multiple Glycine residues enabling a highly flexible conformation and Serine or Threonine providing polar surface area to limit hydrophobic interaction within the peptide or with the component fusion protein moieties, Many peptide linkers described in the literature are rich in glycine and serine, such as repeats of the sequence GGGGS, although an artisan skilled in the art will recognize that other sequences following the general recommendations of Argos (Argos, 1990, J Mol Biol. 20; 211(4):943-58) can also be used. For instance, one of the proteins described herein is contains a linker peptide composed of Glycine and Alanine (SEQ ID NO 15). A flexible linker peptide with a fully extended beta-strand conformation will have an end-to-end length of approximately 3.5 Å per residue. Thus, a linker peptide of 5, 10, 15, 20, 25, or 30 residues will have a maximum fully extended length of 17.5 Å, 35 Å, 52.5 Å, 70 Å, 87.5 Å, or 105 Å respectively. The maximal end-to-end length of the peptide linker can also be a guide for defining the characteristics of a peptide linker in this invention.

Skilled artisans will also recognize that nonpeptide flexible chemical linkers may also substitute for a polypeptide linker of the indicated lengths above, eg. 17.5 Å, 35 Å, 52.5 Å, 70 Å, 87.5 Å, or 105 Å. The goal of a linker peptide within the current invention is to enable attainment of an appropriate conformation and orientation of the individual fusion protein moieties to allow the engagement of the IL-2 Selective Agonist moiety with its cognate receptor and allow the binding of the Fc moiety to the FeRn to enable fusion protein recycling and a prolonged circulating half-life. Many Fc fusion proteins do not require linker peptides, as evidenced by the 8 out of 10 US FDA-approved Fc fusion proteins lacking such peptides listed in Table I. In contrast, Dulaglutide, a fusion of GLP-1 and Fc, contains a 15 residue peptide linker which has a strong influence on bioactivity (Glaesner, U.S. Pat. No. 7,452,966 B2). Prior work in the art on IL-2-Fc fusion proteins indicates that linker peptides are not necessary for bioactivity. IL-2 fusion proteins containing wt IL-2 or IL-2 with the substitution C125S in the Fc-X orientation have been reported to have IL2 bioactivity similar to that of the free 1L2 cytokine without (Gillies, et al., 1992, Proc Natl Acad Sci, 89:1428-32; Gavin, et al., US Patent Application 20140286898 A1) or with (Bell, et al., 2015, J Autoimmun. 56:66-80) peptide linkers. In the X-Fc orientation, Zheng et al, reported IL-2 bioactivity of an IL-2 fusion protein in the X-Fc configuration that was essentially indistinguishable from that of IL-2 itself (Zhen, X. X., et al., 1999, J Immunol. 1999, 163:4041-8). This extensive prior art teaches that fusion of an IL-2 protein with Fc will not require a linker peptide in order to have high IL-2 bioactivity. However, Gavin et al. reported that Fc fusion proteins in the X-Fc configuration containing certain IL-2 variants with altered receptor selectivity have reduced or no bioactivity either without a peptide linker or with a 5 residue peptide linker (Gavin, et al., US Patent Application 20140286898 A1). The work reported in this patent demonstrates that a peptide linker of at least 6 and preferably at least 9 amino acids are necessary for robust IL-2 bioactivity on Tregs, and further shows that the improvement in bioactivity reaches a plateau at 15 amino acids, and is maintained with linkers up to 30 amino acids in length.

Bioassays

Robust and quantitative bioassays are necessary for the characterization of the biological activity of candidate proteins. These assays should measure the activation of the IL2 receptor, measure the downstream functional consequences of activation in Tregs, and measure therapeutically-relevant outcomes and functions of the activated Tregs. These assays can be used the measure the therapeutic activity and potency of IL2 Selective Agonist molecules, and can also be used for measurement of the pharmacodynamics of an IL2 Selective Agonist in animals or in humans. One assay measures the phosphorylation of the signal transduction protein STAT5, measured flow cytometry with an antibody specific for the phosphorylated protein (pSTAT5). Phosphorylation of STAT5 is an essential step in the IL-2 signal transduction pathway. STAT5 is essential for Treg development, and a constitutively activated form of STAT5 expressed in CD4+ CD25+ cells is sufficient for the production of Treg cells in the absence of IL-2 (Mahmud, S. A., et al., 2013, JAKSTAT 2:e23154). Therefore, measurement of phosphorylated STAT5 (pSTAT5) in Treg cells will be recognized by someone skilled in the art as reflective of IL-2 activation in these cells, and will be predictive of other biological outcomes of IL-2 treatment given appropriate exposure time and conditions. Another assay for functional activation measures IL-2-stimulated proliferation of Treg cells. Someone skilled in the art will recognize that Treg proliferation can be measured by tritiated thymidine incorporation into purified Treg cells, by an increase in Treg cell numbers in a mixed population of cells measured by flow cytometry and the frequencies of CD4+CD25+FOXP3+ or the CD4+CD25+ CD127− marker phenotypes, by increased expression in Treg cells of proliferation-associated cell cycle proteins, such as Ki-67, or by measurement of the cell division-associated dilution of a vital fluorescent dye such as carboxyfluorescein succinimidyl ester (CFSE) by flow cytometry in Treg cells. Another assay for functional activation of Tregs with IL-2 is the increased stability of Tregs. pTreg, cells are thought by some to be unstable, and have the potential to differentiate into Th1 and Th17 effector T cells. IL-2 activation of Tregs can stabilize Tregs and prevent this differentiation (Chen, Q., et al., 2011, J Immunol, 186:6329-37). Another outcome of IL-2 stimulation of Tregs is the stimulation of the level of Treg functional effector molecules, such as CTLA4, GITR, LAG3, TIGIT, IL-10, CD39, and CD73, which contribute to the immunosuppressive activity of Tregs.

To develop an IL2 Selective Agonist Fc protein, we initially focused on proteins in the X-Fc configuration because of the short circulating half-lives that have been reported for IL-2 fusion proteins in the Fc-X configuration. The first two proteins produced and tested, one with and one without a linker peptide, unexpectedly showed that the protein with the peptide linker had IL-2 bioactivity and that the protein without the peptide linker had no detectable bioactivity. Both proteins exhibited high binding affinity for IL2RA, indicating that both proteins were properly folded. These results suggested that a linker peptide was necessary for IL-2 receptor activation and bioactivity. A series of additional analogs was then produced to eliminate other variables and to test this hypothesis. The results from these studies led to the discovery of key structure-activity relationships for this therapeutic protein and created novel molecules with the desired activity and pharmaceutical attributes.

The following table provides a list of the preferred species.

| Name | Linker | Fusion partner |
|---|---|---|
| N88RL10AG1 | 10 amino acids | IgG1(N297A) Fc |
| N88RL15AG1 | 15 amino acids | IgG1(N297A) Fc |
| N88RL20AG1 | 20 amino acids | IgG1(N297A) Fc |
| N88RL25AG1 | 25 amino acids | IgG1(N297A) Fc |
| N88RL30AG1 | 30 amino acids | IgG1(N297A) Fc |
| N88RL15G1ED | 15 amino acids | IgG1(E233P/L234A/L235A/G236del) |
| N88RL15G2 | 15 amino acids | IgG2 Fc |
| N88RL15G4(S228P) | 15 amino acids | IgG4 Fc |
| N88RT3AL15AG1 | 15 amino acids | IgG1(N297A) Fc |
| N88RL15HSA | 15 amino acids | HSA (C-terminal) |
| HSAL15N88R | 15 amino acids | HSA (N-terminal) |
| N88GL15AG1 | 15 amino acids | IgG1(N297A) Fc |
| D20HL15AG1 | 15 amino acids | IgG1(N297A) Fc |
| Q126LL15AG1 | 15 amino acids | IgG1(N297A) Fc |
| Q126FL15AG1 | 15 amino acids | IgG1(N297A) Fc |

Formulation

Pharmaceutical compositions of the fusion proteins of the present invention are defined as formulated for parenteral (particularly intravenous or subcutaneous) delivery according to conventional methods. In general, pharmaceutical formulations will include fusion proteins of the present invention in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, ed., Mack Publishing Co., Easton, Pa., 19.sup.th ed., 1995.

As an illustration, pharmaceutical formulations may be supplied as a kit comprising a container that comprises fusion proteins of the present invention. Therapeutic proteins can be provided in the form of an injectable solution for single or multiple doses, as a sterile powder that will be reconstituted before injection, or as a prefilled syringe. Such a kit may further comprise written information on indications and usage of the pharmaceutical composition. Moreover, such information may include a statement that the fusion proteins of the present invention is contraindicated in patients with known hypersensitivity to fusion proteins of the present invention.

The IL-2 selective agonist fusion proteins of this invention can be incorporated into compositions, including pharmaceutical compositions. Such compositions typically include the protein and a pharmaceutically acceptable carrier. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

A pharmaceutical composition is formulated to be compatible with its intended route of administration. The IL-2 selective agonist fusion proteins of the invention is likely that to be administered through a parenteral route. Examples of parenteral routes of administration include, for example, intravenous, intradermal, and subcutaneous. Solutions or suspensions used for parenteral application can include the following components: a sterile diluent such as water for injection, saline solution, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition should be sterile and should be fluid to the extent that easy, syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The maintenance of the required particle size in the case of dispersion may be facilitated by the use of surfactants, e.g., Polysorbate or Tween, Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization, Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the IL-2 selective agonist fusion protein is prepared with carriers that will protect the IL-2 selective agonist fusion protein against rapid elimination from the body, such as a controlled release formulation, including implants and microencapsulated delivery systems, Biodegradable, biocompatible polymers can be used, such as ethylene vinyl acetate, polyanhydrides, polyglycolic acid, collagen, polyorthoesters, and polylactic acid. Such formulations can be prepared using standard techniques.

The pharmaceutical compositions can be included in a container, pack, or dispenser together with instructions for administration.

Administration

Fusion proteins of the present invention will preferably be administered by the parenteral route. The subcutaneous route is the preferred route, but intravenous, intramuscular, and subdermal administration can also be used. For subcutaneous or intramuscular routes, depots and depot formulations can be used. For certain diseases specialized routes of administration can be used. For instance, for inflammatory eye diseases intraocular injection can be used. Fusion proteins can be used in a concentration of about 0.1 to 10 mcg/ml of total volume, although concentrations in the range of 0.01 mcg/ml to 100 mcg/ml may be used.

Determination of dose is within the level of ordinary skill in the art. Dosing is daily or weekly over the period of treatment, or may be at another intermittent frequency. Intravenous administration will be by bolus injection or infusion over a typical period of one to several hours. Sustained release formulations can also be employed, in general, a therapeutically effective amount of fusion proteins of the present invention is an amount sufficient to produce a clinically significant change in the treated condition, such as a clinically significant change in circulating Treg cells, a clinically significant change in Treg cells present within a diseased tissue, or a clinically significant change in a disease symptom.

The data obtained from the cell culture assays and animal studies can be used in formulating a range of dosage for use in humans. The dosage of such compounds lies preferably within a range of circulating concentrations that include the half maximal effective concentration (EC50; i.e., the concentration of the test compound which achieves a half-maximal stimulation of Treg cells) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 as determined in cell culture. Such information can be used to more accurately determine useful doses in humans. Levels in plasma may be measured, for example, by enzyme-linked immunosorbent assays.

As defined herein, a therapeutically effective amount of a IL-2 selective agonist fusion protein (i.e., an effective dosage) depends on the polypeptide selected and the dose frequency. For instance, single dose amounts in the range of approximately 0.001 to 0.1 mg/kg of patient body weight can be administered; in some embodiments, about 0.005, 0.01, 0.05 mg/kg may be administered. The compositions can be administered from one time per day to one or more times per week, or one or more times per month; including once every other day. The skilled artisan will appreciate that certain factors may influence the dosage and timing required to effectively treat a subject, including but not limited to the severity of the disease or disorder, previous treatments, the general health and/or age of the subject, the level of Treg cells present in the patient, and other diseases present. Moreover, treatment of a subject with a therapeutically effective amount of the IL-2 selective agonist fusion protein of the invention is likely to be a series of treatments.

Autoimmune Diseases

Some of the diseases that can benefit from the therapy of this invention have been noted. However, the role of Treg cells in autoimmune diseases is a very active area of research, and additional diseases will likely be identified as treatable by this invention. Autoimmune diseases are defined as human diseases in which the immune system attacks its own proteins, cells, and tissues. A comprehensive listing and review of autoimmune diseases can be found in The Autoimmune Diseases (Rose and Mackay, 2014, Academic Press). Diseases for which there is evidence for a benefit from Treg augmentation includes Graft-vs-Host Disease, Pemphigus Vulgaris, Systemic Lupus Erythematosus, Scleroderma, Ulcerative Colitis, Crohn's Disease, Psoriasis, Type 1 Diabetes, Multiple Sclerosis, Amyotrophic Lateral Sclerosis, Alopecia Areata, Uveitis, Neuromyelitis Optica, and Duchenne Muscular Dystrophy.

Other Fusion Proteins

Because the purpose of the Fc protein moiety in this invention is solely to increase circulating half-life, one skilled in the art will recognize that the IL-2 selective agonist moiety could be fused to the N-terminus of other proteins to achieve the same goal of increasing molecular size and reducing the rate of renal clearance, using the structure-activity relationships discovered in this invention. The IL2 selective agonist could be fused to the N-terminus of serum albumin (Sleep, D., et al., 2013, Biochim Biophys Acta.1830:5526-34), which both increases the hydrodynamic radius of the fusion protein relative to the IL-2 moiety and is also recycled by the FcRN. A skilled artisan would also recognize that the IL2 selective agonist moiety of this invention could also be fused to the N-terminus of recombinant non-immunogenic amino acid polymers. Two examples of non-immunogenic amino acid polymers developed for this purpose are XTEN polymers, chains of A, F, G, P, S, and T amino acids (Schellenberger, V., et. al., 2009, Nat Biotechnol, 27: 1186-90)), and PAS polymers, chains of P, A, and S amino acid residues (Schlapschy, M., et. al., 2007, Protein Eng Des Sel. 20:273-84).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1. Cloning, Expression, and Purification of IL-2 Selective Agonist-IgG Fc Fusion Proteins A cDNA encoding N88RL9AG1 (SEQ ID NO 4) was constructed by DNA synthesis and PCR assembly. The N88RL9AG1 construct was composed of the mouse IgG1 signal sequence, the mature human IL-2 (SEQ ID NO 1) sequence with the substitutions N88R and C125S, a 9 amino acid linker peptide sequence (SEQ ID NO 15), and the Fc region of human IgG1 containing the substitution N297A (SEQ ID NO 2). N88R/IL2 is an IL2 selective agonist with reduced binding to IL2RB and selective agonist activity on IL2Rαβγ receptor-expressing cells (Shanafelt, A. B., et al., 2000, Nat Biotechnol, 8:1197-202). Elimination of the N-linked glycosylation site at N297 on IgG1 Fc reduces Fc effector functions (Tao, M. H., et al., 1989, J Immunol, 143:2595-2601), D20HL0G2 was composed of the mouse IgG1 signal sequence, IL-2 (SEQ ID NO 1) with the substitutions D20H and C125S, and an Fc protein moiety derived from human IgG2 (SEQ ID NO 3). The D20H IL-2 variant has been reported to possess selective agonist activity similar to N88R (Cassell, D. J., et. al., 2002, Curr Pharm Des., 8:2171-83).

These eDNAs were cloned into pcDNA3.1(+) (Life Technologies, Carlsbad, Calif.) using the restriction sites HindIII and NotI. Purified expression vector plasmid containing the construct was transiently transfected into HEK293 cells. HEK293 cells were seeded into a shake flask 24 hours before transfection, and were grown using serum-free chemically defined media. The DNA expression constructs were transiently transfected into 0.1 liter of suspension HEK293 cells. After 24 hours, cells were counted to obtain the viability and viable cell count. The cultures were harvested at day 5 and the conditioned media supernatant was clarified by centrifugation at 3000× g for 15 minutes. The protein was purified by running the supernatant over a Protein A column (GE Healthcare), eluting with 0.25% acetic acid (pH 3.5), neutralizing the eluted protein with 1 M Tris (pH 8.0), and dialyzing against 30 mM HEPES, pH 7, 150 mM NaCl. The samples were then sterile filtered through a 0.2 μm membrane filter and analyzed by SDS PAGE under reducing and nonreducing conditions. The proteins migrated as a disulfide-linked dimer. Protein concentration determined by absorbance using the calculated extinction coefficient of 1.11 mg/ml $cm^{-1}$, and aliquots stored at −80 C.

The cytokines N88R/IL2 and D20H/IL2 are variants of SEQ ID NO 1 and were produced in *E. coli* essentially as described in U.S. Pat. No. 6,955,807 B1, except for the addition of the additional mutation C125S for improved stability.

Example 2. Determination of Receptor-binding Activity of N88RL9AG1 and D20HL0G2

To determine if N88RL9AG1 and D20HL0G2 were properly folded, their affinity to the IL-2 receptor subunits IL2RA and IL2RB was determined by surface plasmon resonance (SPR) using a Biacore T-200 instrument (GE Healthcare). IL2RA and IL2RB extracellular domain proteins and IL-2 protein (R&D Systems, Minneapolis, Minn.) were immobilized on CM-5 Biacore chips by NHS/EDC coupling to final RU (resonance units) values of 30 and 484, respectively. The kinetics of binding to IL2RA was measured at five concentrations of IL2 and N88RL9AG1 ranging from 0.6 nM to 45 nM at a flow rate 50 ul/minute. The kinetics of binding to IL2RB was measured at five concentrations ranging from 16.7 nM to 450 nM for IL2 and from 14 nM to 372 nM for the Fc fusion proteins at a flow rate of 10 ul/minute. The dissociation constants (Kd) were calculated from the kinetic constants using the Biacore evaluation software version 2.0, assuming 1:1 fit for IL-2 and the bivalent fit for N88RL9AG1 and D20HL0G2. Equilibrium Kd values were calculated by the Biacore evaluation software using steady-state binding values.

Binding to IL2RA was detected for both IL-2 and N88RL9AG1. The Rmax value for N88RL9AG1, 14.43, was 5.5 fold higher than that of IL2, 2.62, consistent with the fact that N88RL9AG1 (82,916 g/M) has a greater molecular weight than IL-2 (15,444 g/M). The kon, koff, and Kd values for IL-2 were in the range expected from published SPR values (Table II). The affinity of N88RL9AG1 was approximately 2-fold greater than that of IL2 as determined by both the kinetic and equilibrium methods. Binding of IL2 to IL2RB was detected with an Rmax of 6.19. The values determined for kon, koff, and Kd are within the range reported in the literature, Reported values are $3.1\times10^{-8}$ M (IL2RA) and $5.0\times10^{-7}$ M (IL2RB) (Myszka, D. G., et al., 1996, Protein Sci. 5:2468-78); $5.4\times10^{-8}$ M (IL2RA) and $4.5\times10^{-7}$ (IL2RB) (Shanafelt, A. B., et al., 2000, Nat Biotechnol.18:1197-202); and $6.6\times10^{-9}$ M (IL2RA) and $2.8\times10^{-7}$ M (IL2RB) (Ring, A. M., et al., 2012, Nat Immunol. 13:1187-95). Essentially no binding of N88RL9AG1 to IL2RB was detected, with a slight binding detected at the highest concentration tested (Rmax=0.06), far below that expected based on the molecular weight difference between IL2 and N88RL9AG1 and based on the IL2RA binding results. The D20HL0G2 protein was also tested for binding to IL2RA, and was found to have a Kd of $8.3\times10^{-9}$ M, similar to that of N88RL9AG1. Thus, SPR binding studies indicated that both N88RL9AG1 and D20HL0G2 proteins bind to IL2RA, indicating that the proteins are properly folded.

Example 3. Bioactivity of N88RL9AG1 and D20HL0G2 on T Cells

The bioactivity of N88RL9AG1 and D20HL0G2 on T cells was determined by measuring phosphorylated STAT5 (pSTAT5) levels in specific T cell subsets. Levels of pSTAT5 were measured by flow cytometry in fixed and permeabilized cells using an antibody to a phosphorylated STAT5 peptide. Treg cells constitutively express CD25, and cells that are in the top 1% of CD25 expression levels are highly enriched for Treg cells (Jailwala, P., et al., 2009, PLoS One. 2009; 4:e6527; Long, S. A., et al., 2010, Diabetes 59:407-15). Therefore, the flow cytometry data was gated into $CD25^{high}$ (the top 1-2% of CD25 expressing cells) and $CD25^{-/low}$ groups for the Treg and CD4 effector T cell subsets, respectively.

Cryopreserved CD4+ T cells (Astarte Biologics, Seattle, Wash.) were defrosted, washed in X-VIVO 15 (Lonza, Allendale, N.J.) media containing 1% human AB serum (Mediatech, Manassas, Va.) and allowed to recover for 2 hours at 37 C. Cells were then distributed in 0.1 ml into 15×75 mm tubes at a concentration of $5\times10^6$ cells/ml. Cells were treated with varying concentrations of IL-2 or Fc fusion proteins for 10 minutes at 37 C. Cells were then fixed with Cytofix Fixation Buffer at 37 C for 10 minutes, permeabilized with Perm Buffer III (BD Biosciences, Santa Clara, Calif.) for 30 minutes on ice, and then washed. Cells were then stained with a mixture of anti-CD4-Pacific Blue (BD Biosciences, Santa Clara, Calif.), anti-CD25-AF488 (eBioscience, San Diego, Calif.), and anti-pSTAT5-AF547 (BD Biosciences) antibodies at concentrations recommended by the manufacturer for 30 minutes at 20 C, washed, and flow cytometry data acquired on an LSRII instrument (BD Biosciences). Data was analyzed using Flowjo analysis software (Flowjo, Ashland, Oreg.).

Figure 3A:
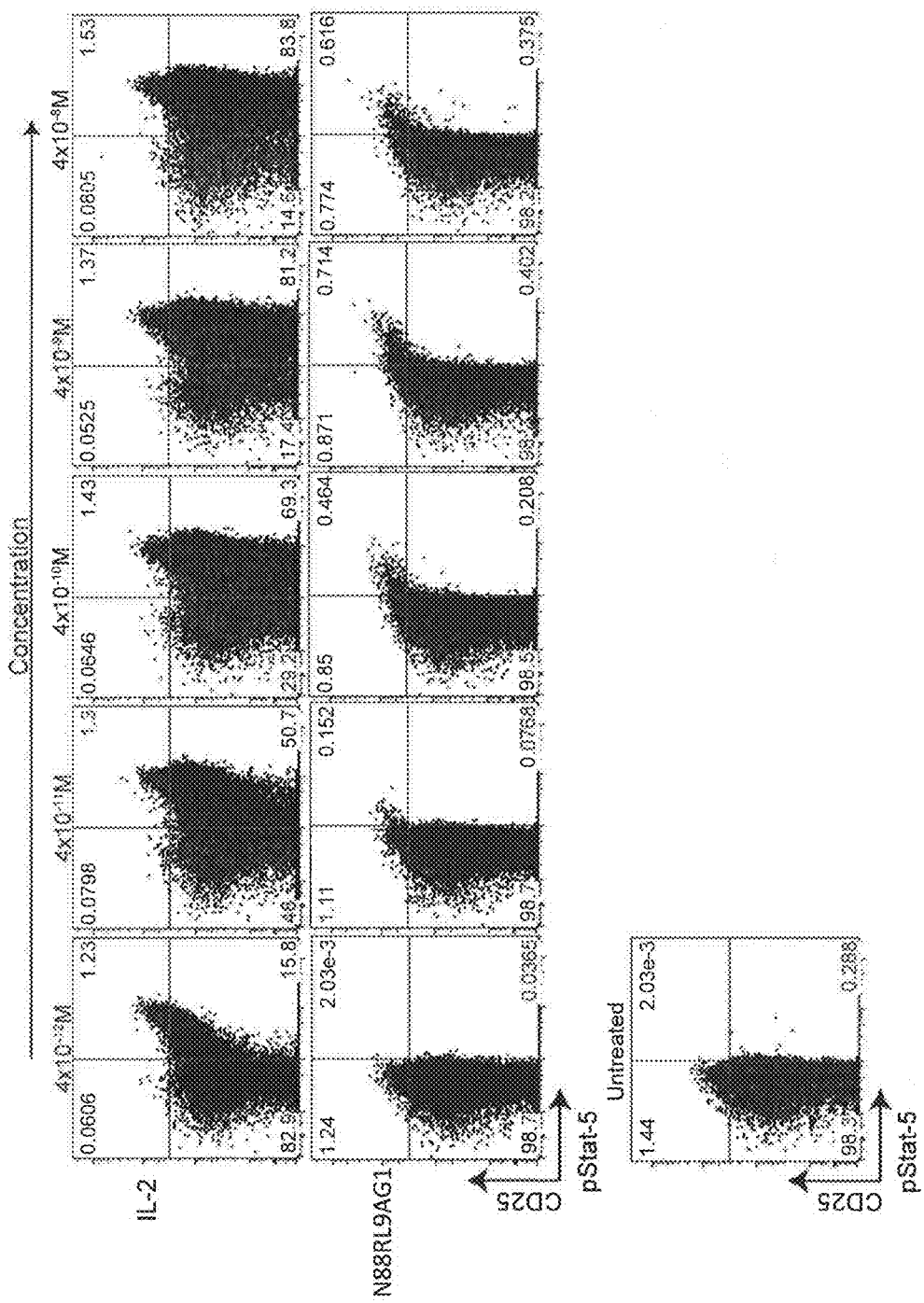
FIGS. 3A-3C show a dose-response of IL-2 and N88RL9AG1 stimulated STAT5 phosphorylation in CD4+ T cells as measured by flow cytometry. Cells were treated with the IL-2 or N88RIL2-Fc at the concentrations indicated on the top for 10 minutes at 37 C, fixed, permeabilized, stained with antibodies, and then subjected to flow cytometry analysis as described in Example 3. Cells gated as CD4+ are shown, and cells further gated with respect to CD25 and pSTAT5 as shown in each of the 4 quadrants. The numbers in each quadrant indicate the percentage of CD4+ cells in each gate. Cells in the upper quadrants represent the highest 1-2% of CD25 expressing cells, a population enriched for Treg cells, and cells in the right-hand quadrants are pSTAT5+.

The results with N88RL9AG1 in this assay indicated that compared to IL-2 N88RL9AG1 had remarkable selectivity for the Treg population (FIG. 3A). N88RL9AG1 activated less than 1% of CD4+ cells, with very strong selectivity for $CD25^{high}$ cells. In contrast, IL-2 activated over 80% of CD4+ T cells at a concentration of 40 nM, with a high proportion of the pSTAT5+ cells expressing low levels or no CD25, Even at 4 pM, the lowest concentration tested, IL-2 still stimulated significant pSTAT5 levels in both $CD25^{-/low}$ cells and $CD25^{high}$ cells.

Figure 3B:
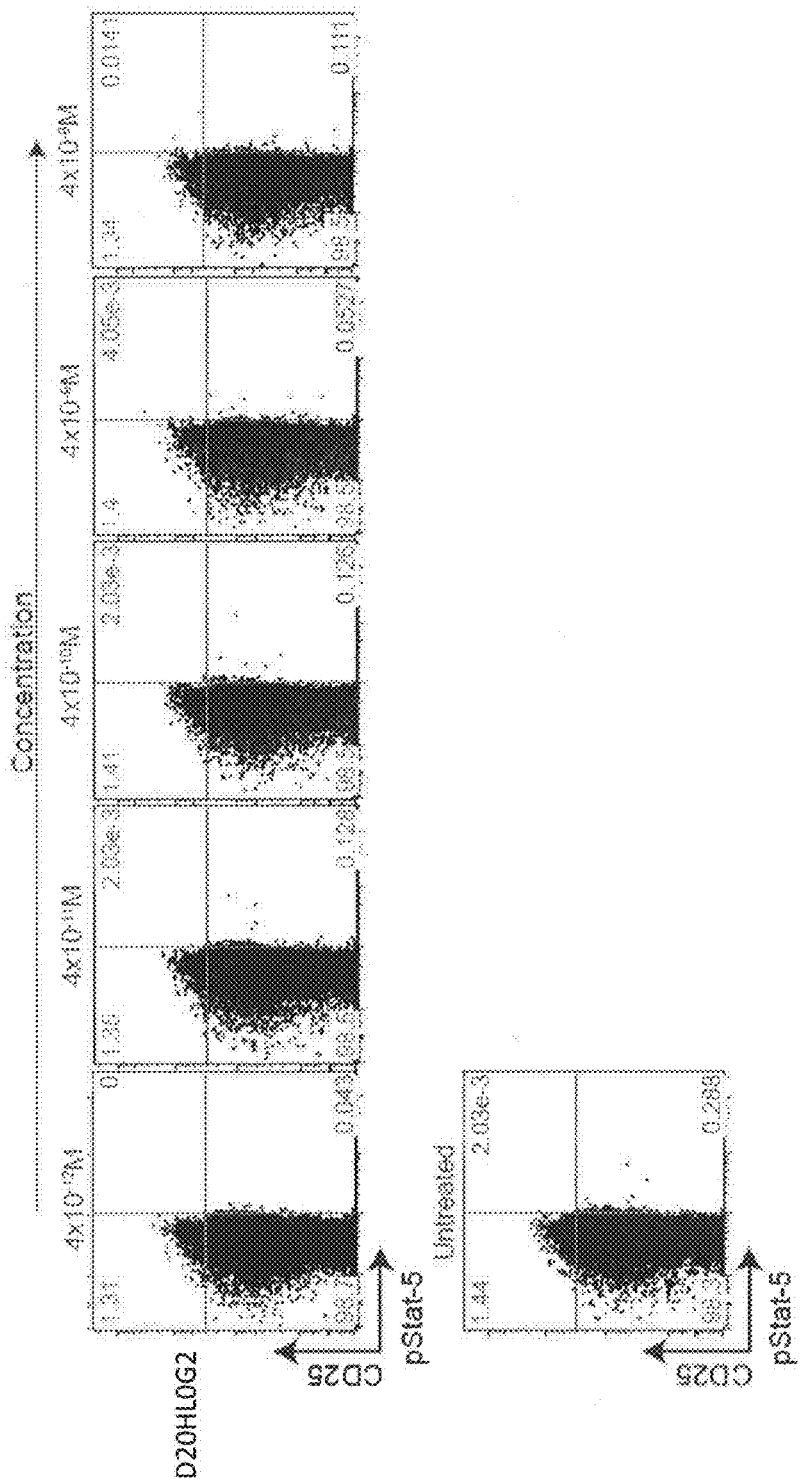
Figure 3C:
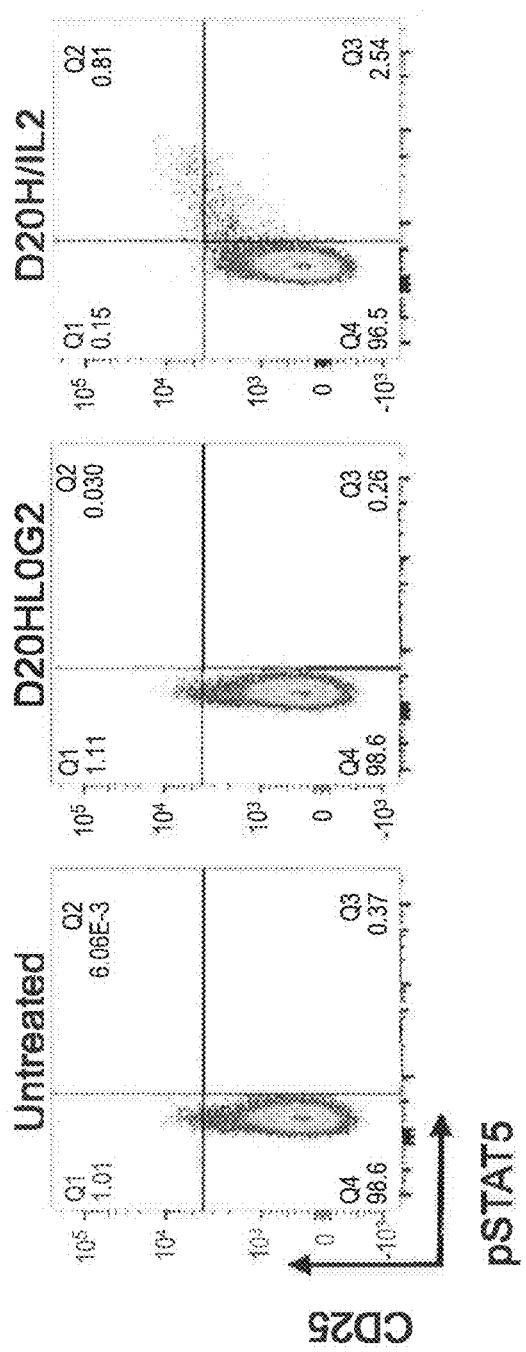
Figure 4:
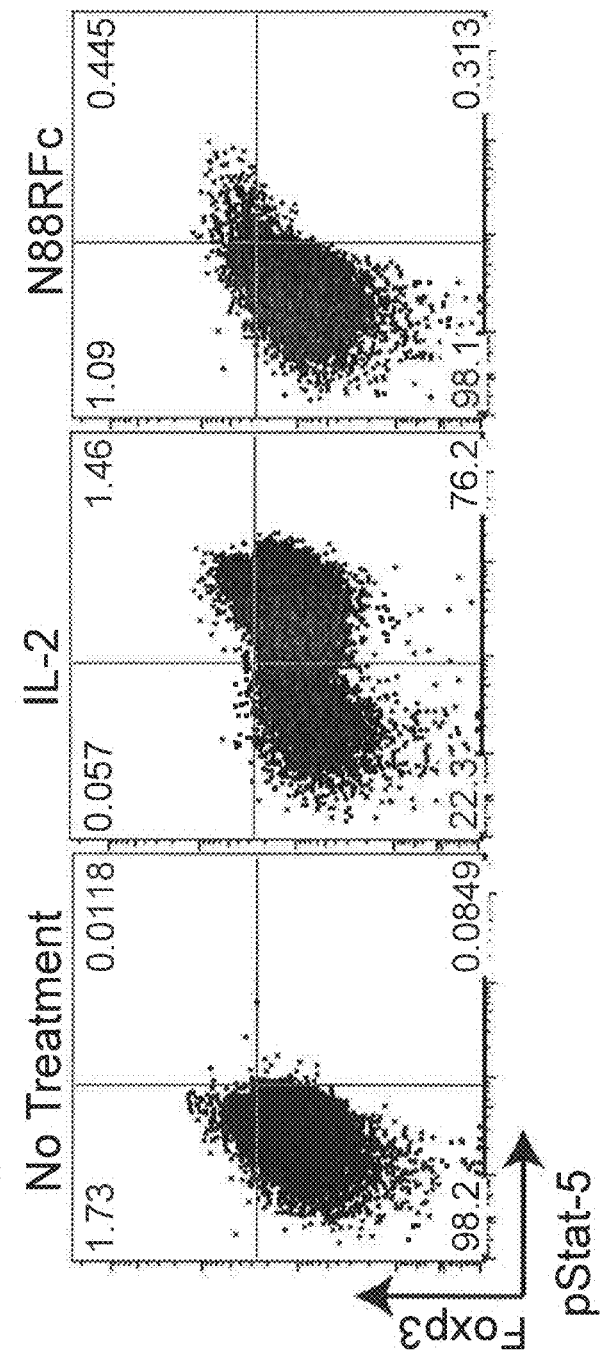
FIG. 4 shows that CD4+ T cells treated with N88RL9AG1 exhibited stimulation of pSTAT5 levels in cells expressing high levels of FOXP3. Cells were treated with $4\times10^{-9}$ M IL-2 or N88RL9AG1 and then analyzed as described in Example 3. The majority of pSTAT5+ cells treated with N88RL9AG1 were also FOXP3+, whereas pSTAT5+cells treated with IL-2 were both FOXP3− and FOXP3+, with the majority being FOXP3−.

D20HL0G2 was then tested for activity in the CD4+ T cell pSTAT5 assay. Unexpectedly, D20HL0G2 had no activity in this assay (FIG. 3B). An additional control with $10^{-8}$ M D20H/IL2 cytokine (the variant IL-2 cytokine not fused to Fc) showed robust and selective pSTAT5 activation of $CD25^{high}$ cells (FIG. 3C). The lack of activity with D20HL0G2 was especially surprising given that D20HL0G2 bound to IL2RA with a Ind similar to that of IL-2 and N88RL9AG1, indicating it was properly folded, To confirm that the $CD25^{high}$ cells selectively activated by N88RL9AG1 were Tregs, activated cells were co-stained for both pSTAT5 and FOXP3, another molecular marker for Treg cells. CD4+ cells were treated with 4 nM IL-2 or N88RL0AG1, fixed, and permeabilized as described above for pSTAT5 staining, and then were subsequently treated with 1 ml FOXP3 Perm Buffer (BioLegend, San Diego, Calif.) for 30 min at room temperature, and then washed and resuspended in FOXP3 Perm Buffer. Permeabilized cells were stained with a mixture of anti-FOXP3-eFluor450, anti-CD25-AF488 (eBioscience, San Diego, Calif.), and anti-pSTAT5-AF547 (BD Biosciences) antibodies for 30 minutes at 20 C, washed, and analyzed by now cytometry. The results of this experiment indicated that a high proportion of N88RL9AG1-treated cells with activated STAT5 (pSTAT5+ cells) were also expressing high levels of FOXP3. This result provides further evidence that the activated cells are highly enriched for Treg cells. In contrast, IL-2 treated pSTAT5+ cells were both FOXP3+ and FOXP3-, with the majority being FOXP3- cells.

Figure 5A:
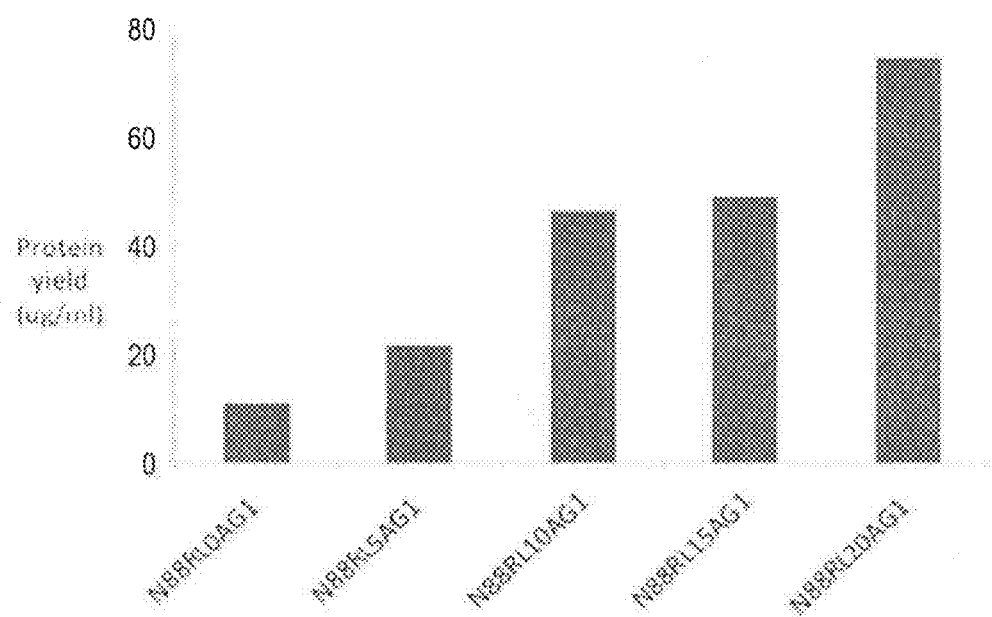
FIGS. 5A-5B show the protein yields of different Fc fusion constructs produced in HEK293 cells. Proteins were expressed in parallel in an optimized transient expression system and purified as described in Example 1. Results are expressed as the final yield of purified protein from 30 ml cultures.
Figure 5B:
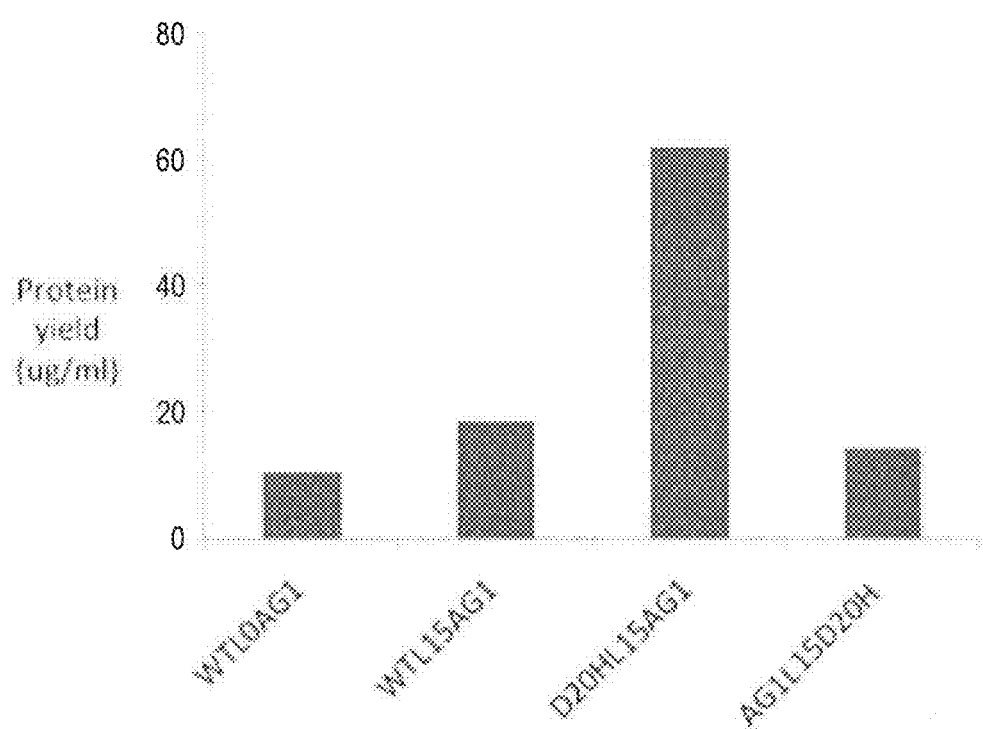

Example 4. Determination of Structure-activity Relationships Important for Bioactivity The unexpected results described in Example 3 suggested that the IL2 bioactivity detected with N88RL9AG1 but not with D20HL0G2 was due to the presence of a linker peptide. To verify this finding and to eliminate the contribution of other variables, such as the isotype of the Fc moiety and the selectivity mutation in the IL-2 moiety, a panel of analogs, ail using the IgG1 N297A Fc, were designed and produced (TABLE III).

cDNAs were constructed and proteins expressed and purified as described in Example 1, except that the C-terminal Lysine residue of the Fc was deleted in all constructs and that the production cell cultures were in a volume of 30 ml instead of 100 ml. All proteins were recovered in good yield. In fact, comparison of the yields of the N88R/IL2 series of molecules indicated a clear trend of increasing protein yield with increasing peptide linker length, with N88RL20AG1 (with the longest peptide linker) recovery 6.8 fold higher than N88RL0AG1 (with no peptide linker) (FIG. 5A). The basis for the increased yields of linker peptide-containing proteins is not yet clear, but could be due to increased expression level, increased secretion rate, increased protein stability, or increased purification efficiency. Interestingly, the yield of WTL15AG1 was only marginally higher (1.8 fold) than that of WTL0AG1, compared to a 4.5 fold higher yield of N88RL15AG1 compared to N88RL0AG1. D20HL15AG1 yield was similar to N88R1-15AG1 yield, indicating the IL-2 selectivity mutation has no significant effect on yield, and both of these proteins had significantly higher yields (4.3 fold and 3.4 fold, respectively) than AG1L15D20H (FIG. 5B). Collectively, these results indicated that increasing peptide linker length was associated with higher protein yield of N88R/IL2 containing Fc fusion proteins, that the yield of Fc fusion proteins containing wt IL-2 was much less sensitive to the presence of a linker peptide, and IL-2-Fc fusion proteins in the X-Fc configuration are produced.

These purified proteins were tested in a human T cell pSTAT5, bioassay essentially as described in Example 3, except that human CD3+ T cells (negatively selected) were used instead of CD4+ cells, and the cells were incubated with test proteins for 20 min rather than 10 min.

Figure 6A:
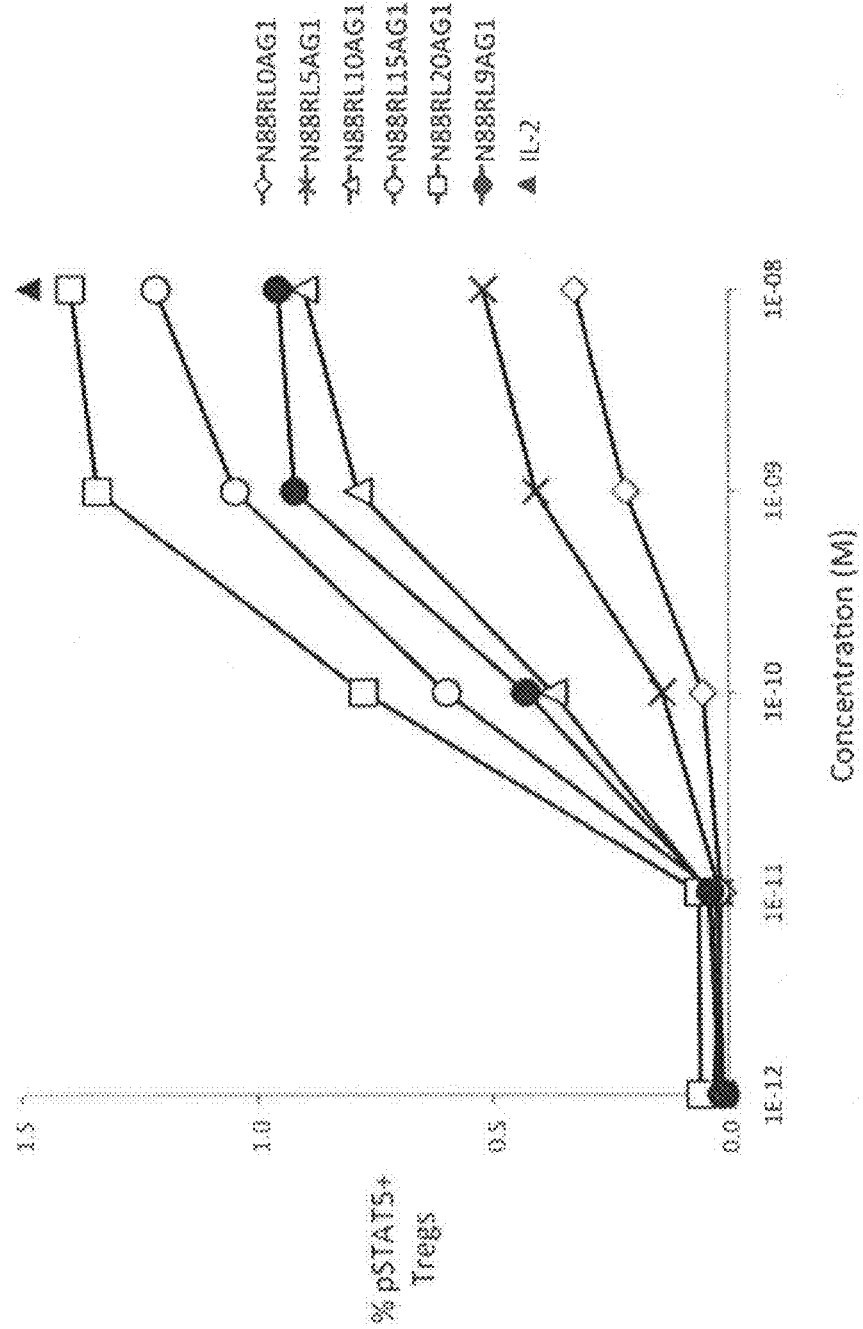
FIGS. 6A-6B show the dependence of IL-2 bioactivity on peptide linker length in N88R/IL2-Fc fusion proteins.

The results from the N88R/IL2 series of molecules showed that bioactivity in the Treg-enriched population was dramatically influenced by peptide linker length (FIG. 6A). The pSTAT5 signal (% pSTAT5+ cells) in the Treg population increased progressively with increasing peptide linker length. This increased bioactivity was reflected both in the maximal pSTAT5 signal at $10^{-8}$ M test protein and by the EC50 values (TABLE IV). N88RL20AG1, the protein with the longest peptide linker, showed a 4.2 fold increase in the maximal pSTAT5 signal over N88RL0AG1. Because the N88RL0AG1 pSTAT5 signal did not reach 50% of IL-2 activation at its highest concentration ($10^{-8}$ M), it was not possible to determine fold improvement in EC50 of the proteins containing linker peptides over N88RL0AG1. However, based on N88RI-20AG1 EC50 and the highest concentration of N88RL0AG1 tested, it can be estimated that N88RL0AG1 will exhibit a >100 fold lower EC50 than N88RL0AG1.

Figure 6B:
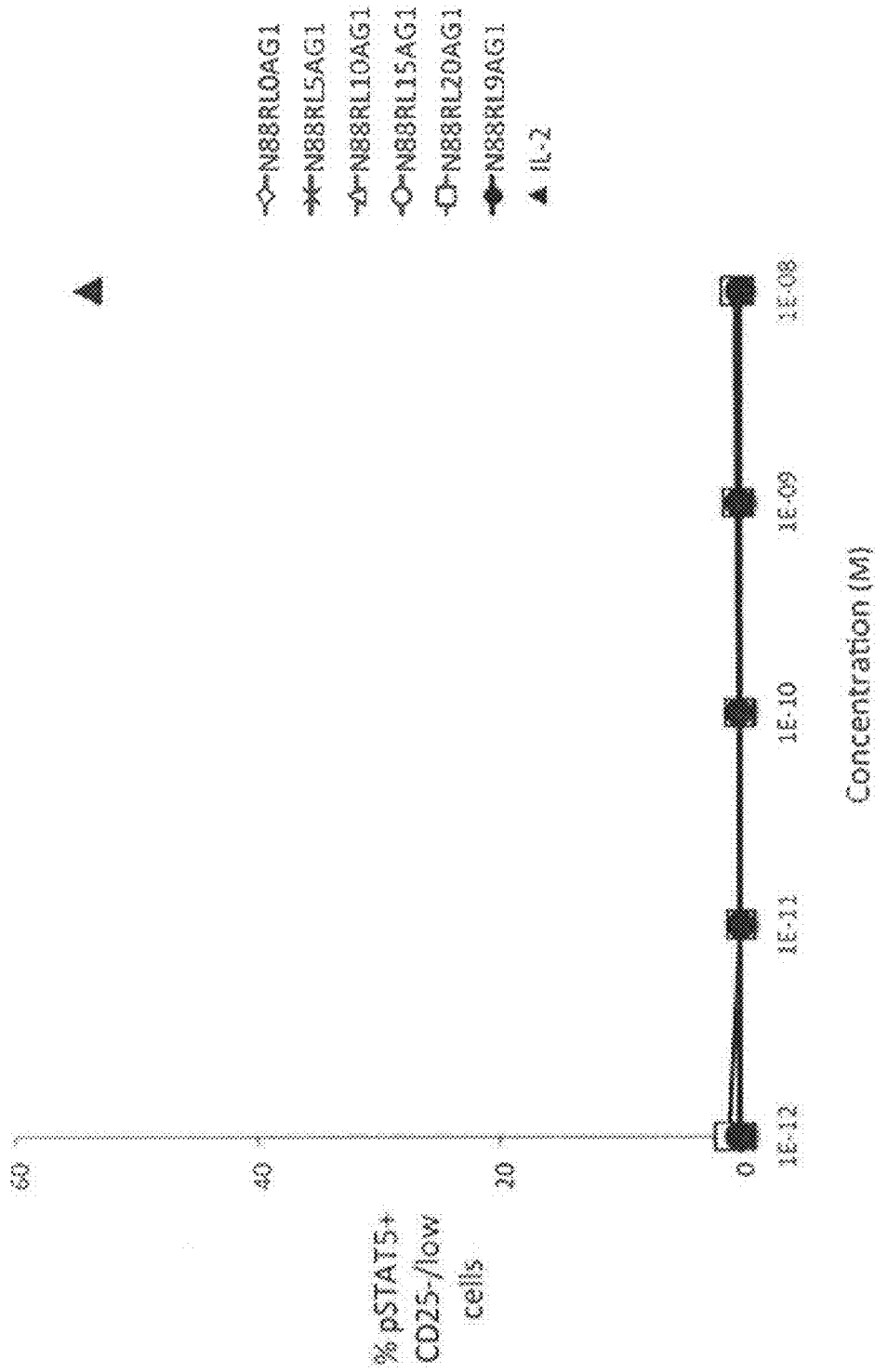

As expected, there was essentially no detectable activity of any of the N88R/IL2 molecules on the $CD25^{-/low}$ population, while $10^{-8}$M IL-2 stimulated pSTAT5 activity in 54.2% of the $CD25^{-/low}$ cells (FIG. 6B).

Figure 7:
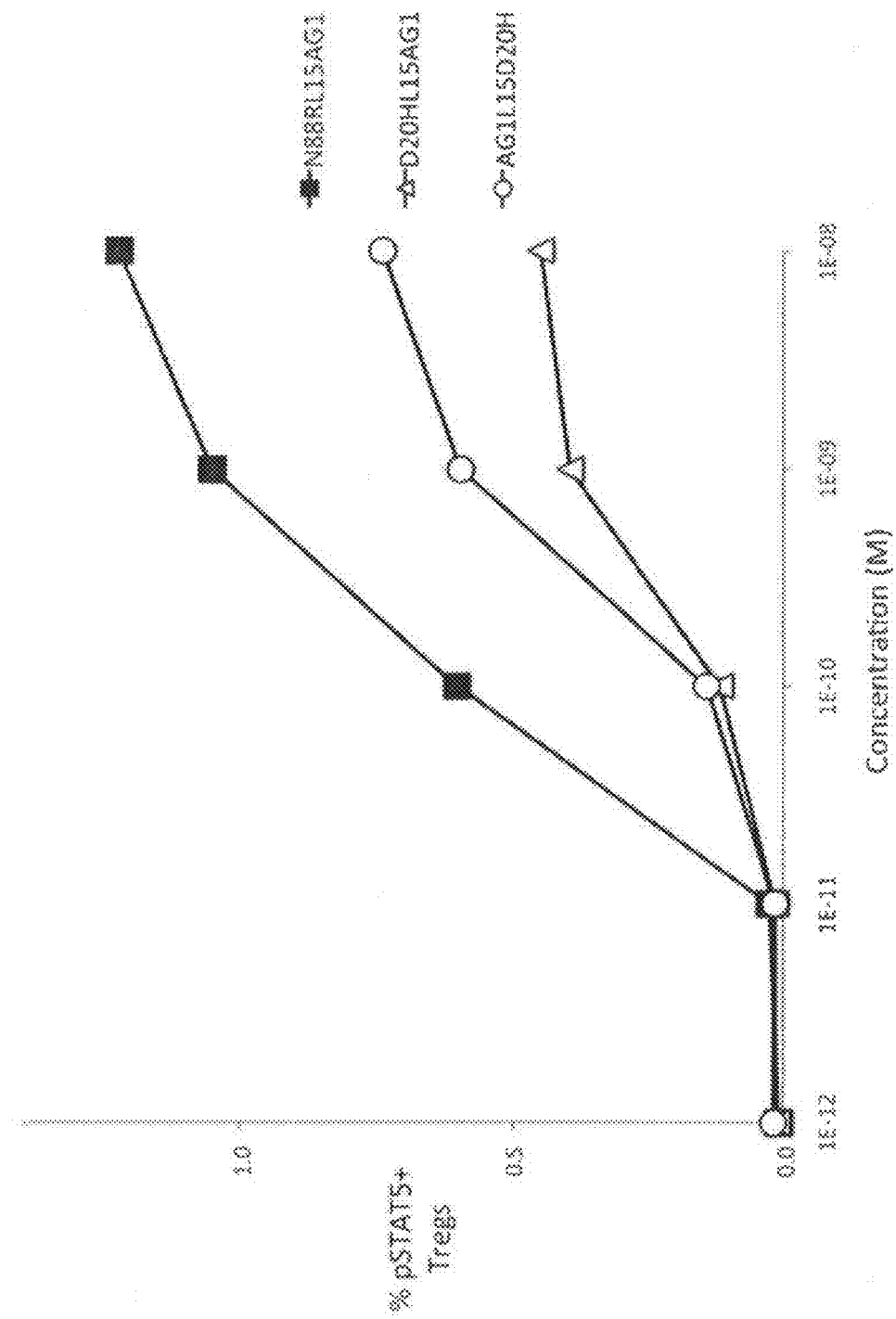
FIG. 7 shows the bioactivity of D20H/IL2-Fc fusion proteins in human Tregs. The potency of D20HL15AG1 is substantially less than that of N88RL15AG1, and D20HL15AG1 (X-Fc configuration) and AG1L15D20H (Fc-X configuration) have similar potencies. All 3 proteins have a 15 residue peptide linker.

The comparison of WTL0AG1 and WTL15AG1 showed that linker peptides have a much less significant effect on wt IL-2-Fc fusion proteins than N88R/IL2-Fc fusion proteins (FIG. 7). In the Treg subpopulation, both WTL0AG1 and WTL15AG1 had significant bioactivity, and in fact stimulated an approximately 2-fold higher maximum level of pSTAT5 phosphorylation than IL-2. However, WTL0AG1 and WTL15AG1 also stimulated large pSTAT5 signals in $CD25^{-/low}$ cells at an approximately 10 fold higher concentration. WTL15AG1 and WTL0AG1 exhibited an approximately 10 fold difference in EC50 values in both the Treg and the $CD25^{-/low}$ cell populations.

Figure 8A:
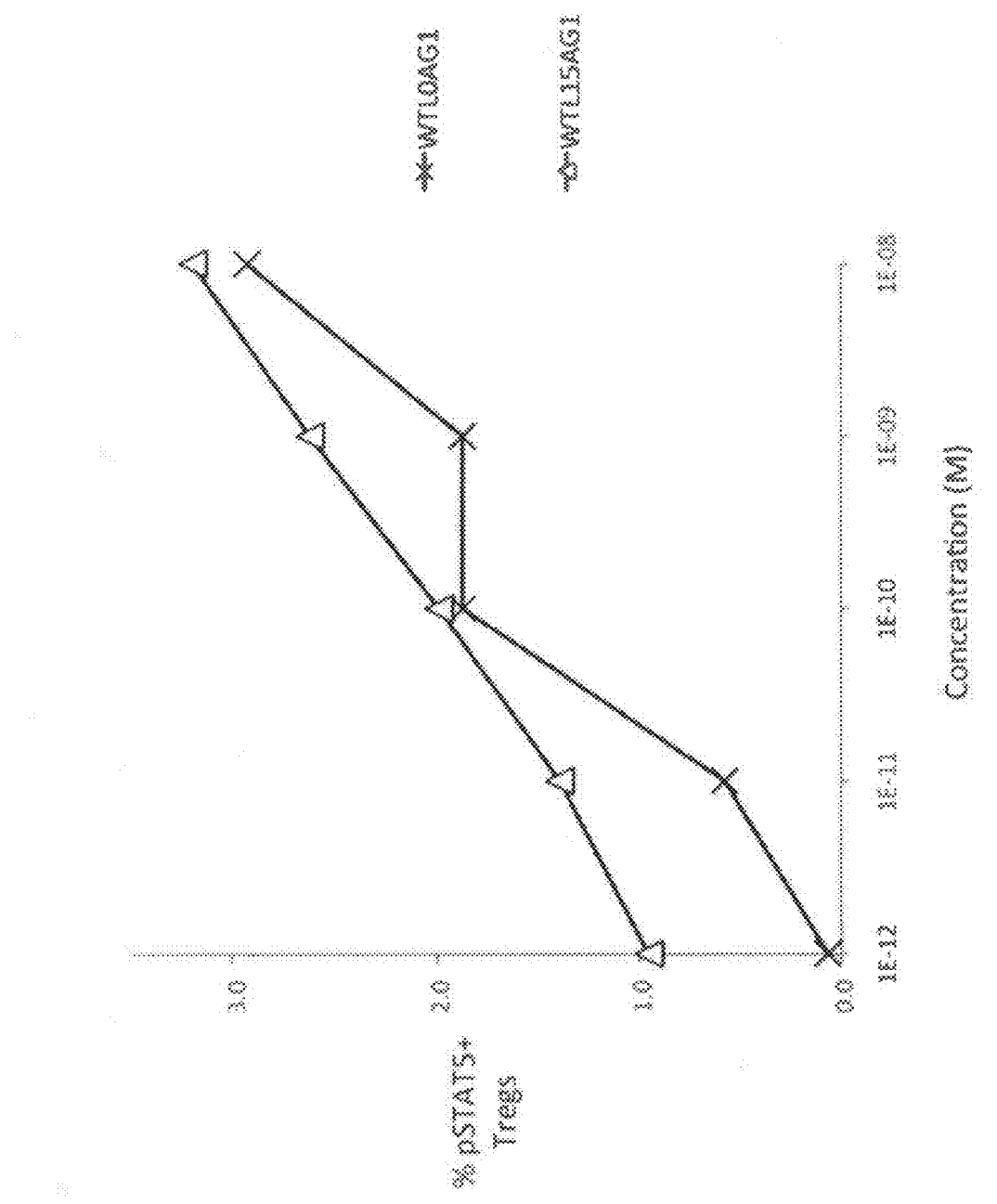
FIGS. 8A-8B show the bioactivity of wt IL-2-Fc pSTAT5 activity with and without a 15 residue peptide linker. IL-2 bioactivity is only modestly enhanced by a 15 residue peptide linker in both Tregs (FIG. 8A) and in CD25$^{-/low}$ cells (FIG. 8B).
Figure 8B:
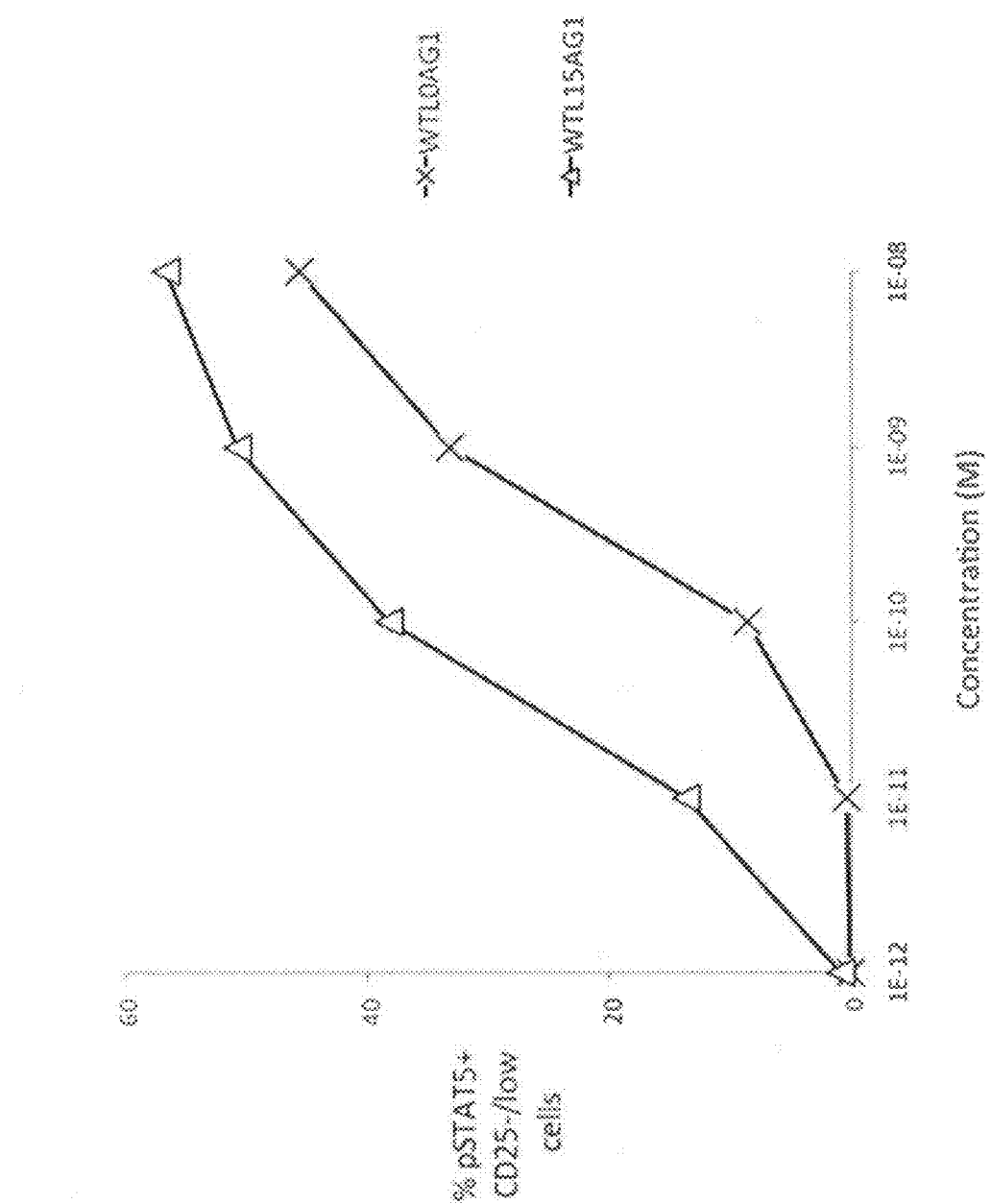

The maximum pSTAT5 signal of D20HL15AG1 in Tregs was significantly less than that of N88RL15AG1 (FIG. 8). This suggests that the lack of any detectable activity in Example 3 with D20HL0G2 was due in part to a lower activity of the D20H/IL2 moiety in the context of an Fc fusion protein compared to the N88R/IL2 moiety. The activity of AG1L15D20H was slightly higher than that of D20HL15AG1, indicating that the configuration of the IL-2 moiety in the Fc fusion protein (ie., X-Fc vs Fc-X) did not have a major effect on Treg bioactivity.

Collectively, these results define key features of N88R/IL2-Fc fusion proteins necessary for optimal bioactivity. N88R/IL2-Fc proteins require a linker peptide for optimal Treg bioactivity, with a trend of increasing bioactivity with increasing linker peptide length. Second, in line with the work of others, linker peptides have a more modest effect on the bioactivity of Fc fusion proteins containing wt IL-2. These differing requirements for a linker peptide may a consequence of the fact that N88R/IL2 is deficient in binding to IL2RB, which could possibly result in more stringent requirements for receptor engagement and increasing the sensitivity to steric hindrance from the Fc fusion protein partner. These results also define the most potent IL2 Selective Agonist-Fc fusion proteins.

Example 5. Selectivity of IL2 Selective Agonist-Fc Fusion Proteins in Human PBMC To determine the selectivity of N88R/IL2-Fc fusion proteins in a broader biological context, an assay was developed to measure STAT5 activation across all key immune cell types in crude unfractionated human PBMC. Human PBMC were isolated by Ficoll-Hypaque centrifugation from a normal volunteer. $10^6$ PBMC were suspended in X-VIVO15 media with glucose (Lonza) and 10% FBS (Omega), and were treated with $10^{-8}$ M test proteins for 20 min at 37° C. Cells were then treated with Foxp3/Transcription Factor Staining Buffer Set (EBIO) according to the manufacturer's instructions. Cells were then fixed with Cytofix buffer and permeabilized with Perm Buffer III as described in Example 3. Fixed and permeabilized cells were then washed with 1% FBS/PBS and stained with antibody mixture for 60 minutes at room temperature in the dark. Stained cells were then washed in 1% FBS/PBS, resuspended in PBS, and analyzed on a Fortessa flow cytometer (BD Biosciences). The antibody mix consisted of: anti-CD4-PerCP-Cy5.5 (BD, #560650), anti-pSTAT5-AF-488 (BD, #612598), anti-CD25-PE (BD, #560989), anti-CD56-PE-CF594 (BD, #562328), anti-FOXP3-AF647 (BD, #560889), anti-CD3-V450 (BD, 560366), and anti-CD8-BV650 (Biolegend, #301041). This staining procedure enabled monitoring of pSTAT5 levels in 7 key immune cells types.

Cell phenotypes were defined as follows: Treg CD3+, CD4+, Foxp3+, $CD25^{high}$, CD8−, CD56−; activated CD4 Teff cells: CD3+, CD4+, Foxp3−, $CD25^{high}$, CD8−, CD56−; CD4 Teff cells: CD3+, CD4+, Foxp3−, $CD25^{low}$, CD8−, CD56−; NKT cells: CD3−, CD4−, Foxp3−, $CD25^{low}$, CD8−, CD56+; NK cells: CD3−, CD4−, Foxp3−, $CD25^{low}$, CD8−, CD56+; B cells: CD3−, CD4−, Foxp3−, $CD25^{low}$, CD8−, CD56−.

Figure 9:
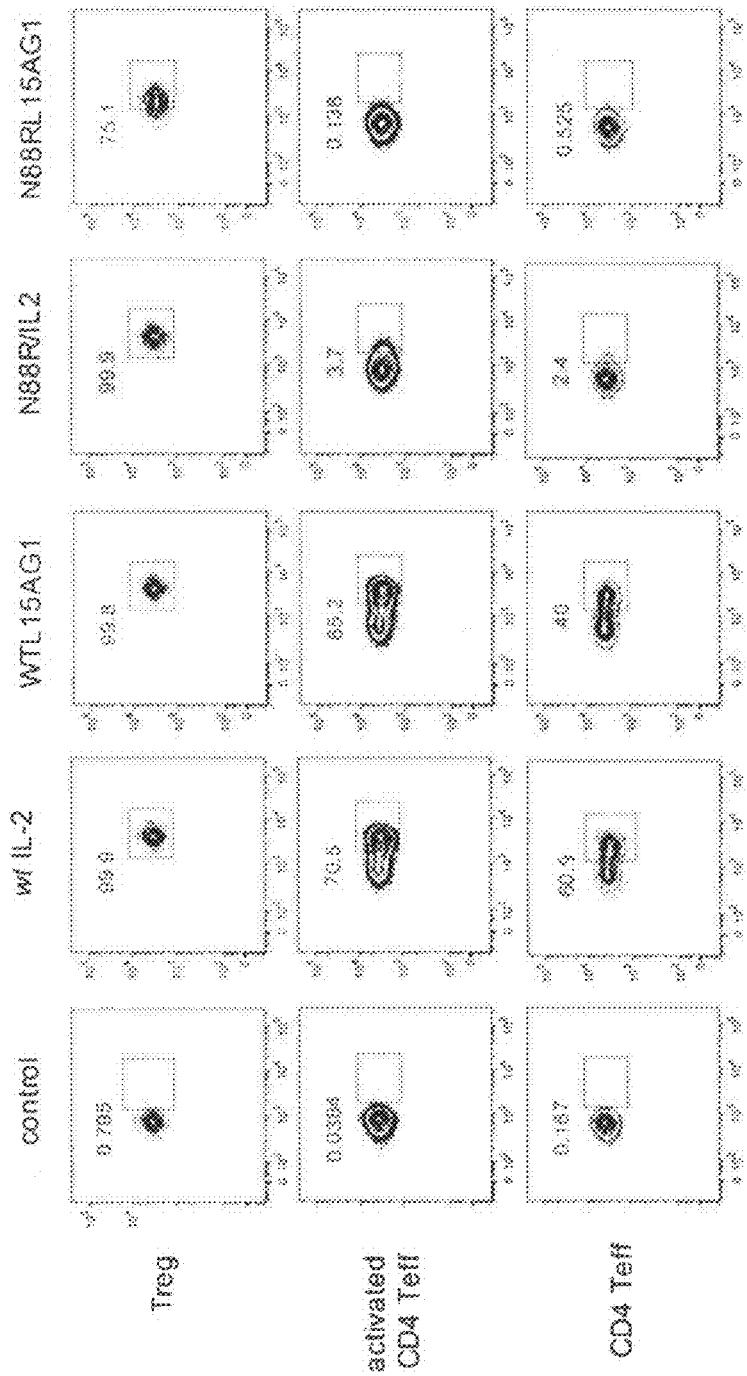
FIG. 9. Selectivity of IL-2 and IL-2 Selective Agonist proteins on 7 different immune cell types in human PBMC. N88RL15AG1 is highly selectivity for Tregs compared to wt IL-2 and WTL15AG1 and shows greater selectivity in multiple cell types than N88R/IL2.
Figure 9:
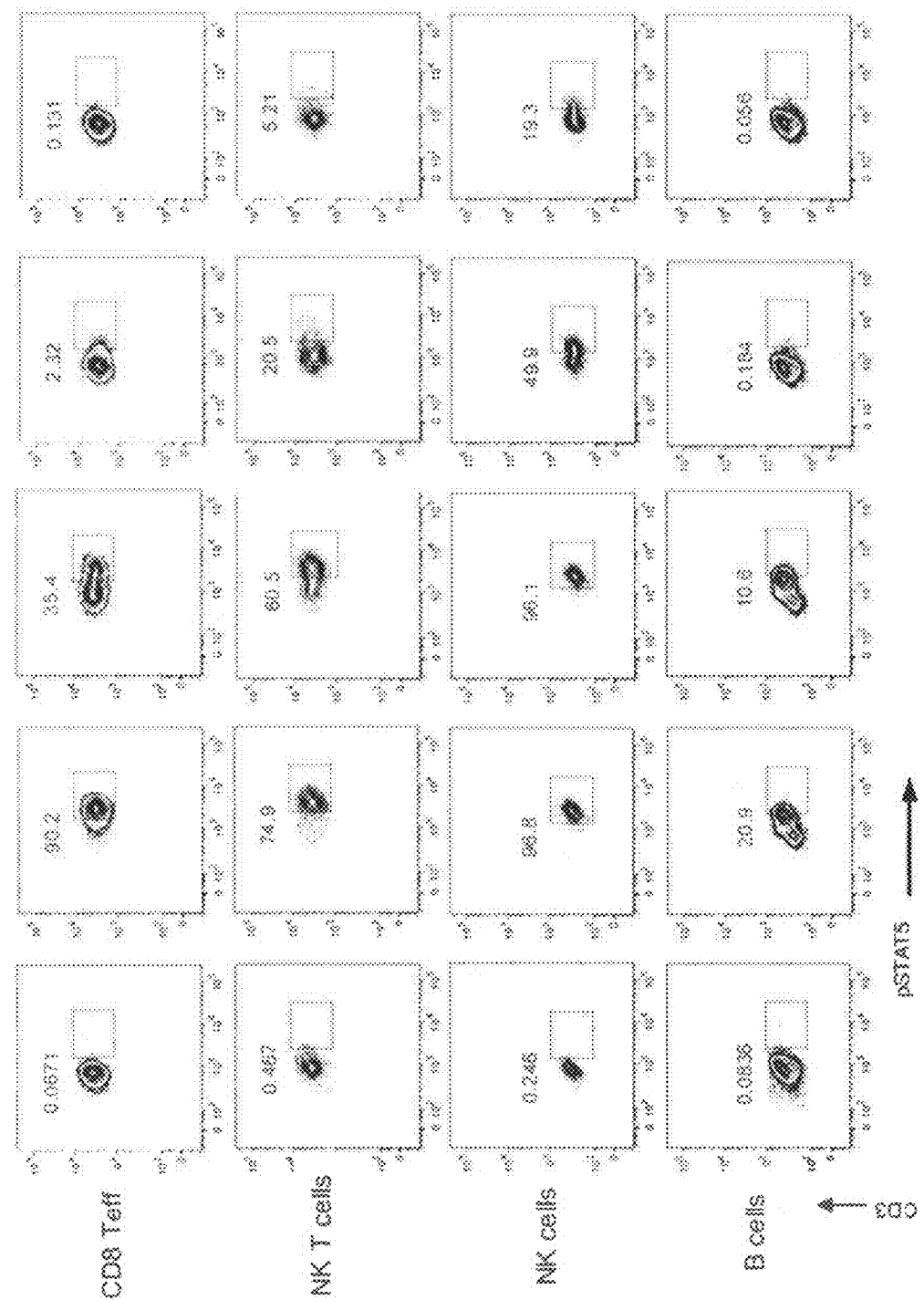

Proteins were tested in this assay at a concentration of $10^{-8}$ M. The results, shown in FIG. 9 and summarized in TABLE V, show that N88RL15AG1 exhibited remarkable selectivity compared to wt IL2 and WTL15AG1, both of which activated pSTAT5 in large fractions of all the cell populations. N88RL15AG1 stimulated pSTAT5 signal in the Treg population at close to the level of wt IL-2, with insignificant activation of the other cell types with the exception of NK cells. Additional analysis (not shown) showed that the pSTAT5+ NK cells were $CD25^{high}$, which is characteristic of NK-$CD56^{bright}$ cells, NK cell subpopulation which also has immunoregulatory activity (Poli, A, et al., 2009 Immunology. 126(4):458-65). Several cell types that had low-level pSTAT5 signals with N88R/IL2 (activated CD4 Teff cells, CD4 Teff cells, NK T cells, and NK cells) exhibited no or lower pSTAT5 signals with N88RL15AG1. These results demonstrate the activity and high selectivity of N88RL15AG1 for Tregs in a complex biological milieu.

Example 6. Exploration of Additional Structure-function Relationships Important for Bioactivity The results presented in Example 5 indicated a strong requirement for a linker peptide of between 6 and 20 amino acids in length for robust bioactivity of N88R/IL-2 Fc fusion proteins, with increasing linker peptide length associated with increasing bioactivity. To determine if even longer linker peptides promote increased bioactivity, additional protein constructs with peptide linker lengths of 25 and 30 amino acids were prepared as described in Example 1, and tested in the T cell pSTAT5 bioactivity assay as described in Example 3 along with independent preparations of N88RL15AG1 and N88RL20AG1. The results of this experiment showed that increasing the peptide linker to 25 (N88RL25AG1) or 30 (N88RL30AG1) amino acids did not result in greater bioactivity on CD25hi cells than the protein with a 20 amino acid linker (Table VII). These results, along the the results presented in Example 4, indicate that the ability of peptide linkers to promote IL-2 bioactivity plateaus at a length of 15-20 amino acids, and that longer linker peptides do not promote further increases in bioactivity.

Alternative Fc fusion partners that could increase circulating half-life and that are deficient in Fc effector functions were assessed. IgG1 Fc with the mutations E233P/L234A/L235A/G236del (SEQ ID NO. 22), IgG2 Fc (SEQ ID NO. 23), and Ig64 Fc with the hinge mutation S228P which stabilizes the Fc dimer (SEQ ID NO. 24) were similarly prepared and tested. Furthermore, torsion proteins in which IL2/N88R was fused to human albumin, either to the N-terminus (N88RL15HSA, SEQ ID NO. 25) or the C-terminus (HSAL15N88R, SEQ ID NO. 26) of human albumin were prepared and tested. Although all proteins were bioactive on CD25hi cells, none of these fusion proteins exhibited bioactivity greater than that observed for N88RL15AG1 (Table VIII).

The effect of different IL-2 selectivity mutations was examined on the backbone of the IgG1 N297A Fc fusion (Table IX). Proteins with the selectivity mutations N88G and Q126F had less bioactivity on CD25hi cells than N88R at $10^{-8}$ M, the highest concentration tested, while exhibiting no bioactivity on CD25-/low cells (data not shown). The protein with the substitution N88I had no activity on either cell type. This may indicate that the original report of selective agonist activity for this variant was erroneous, or alternatively it may indicate that it is not active within the context of an Fc fusion protein, Proteins with the substitution Q126L had greater bioactivity than N88R, as reflected by a greater pSTAT5 response at the highest concentration tests on CD25hi cells, although this was accompanied by a modest increase in activation of CD25-/low expressing cells at the $10^{-8}$ M (data not shown). These results suggest that Q126L/IL2 is a more potent selective agonist, with higher bioactivity on both CD25hi and CD25-/low cells.

Finally, the impact of eliminating the O-linked glycosylation site at Threonine 3 of the IL2/N88R moiety was assessed by preparing the variant N88RT3AL15AG 1. The O-linked glycosylation site in IL-2 is not required for bioactivity (Robb, R. J., et al., 1984, Proc Natl Acad Sci USA. 81:6486-90), and eliminating this glycosylation site should result in a completely aglycosylated protein, which would possess fewer post-translational modifications contributing to product heterogeneity. The variant N88RT3AL15AG1 was prepared and tested, and shown to have bioactivity on CD25hi cells similar to that of N88RL15AG1 (Table IX).

TABLES

TABLE I

TABLE I. US FDA-approved Fc fusion proteins and their characteristics

| DRUG | Fc Isotype | Fusion Partner | N vs C fusion | Linker Peptide | Half-life (days) |
|---|---|---|---|---|---|
| Romiplostim | G1 | TPO-R peptide | C | Y | 3.5 |
| Etanercept | G1 | P75 TNFa-R | N | N | 4.3 |
| Alefacept | G1 | LFA3 | N | N | 10.1 |
| Rilonacept | G1 | IL1-R | N | N | 8.6 |
| Abatacept | G1 | CTLA4 | N | N | 16.7 |
| Belatacept | G1 | CTLA4 (mut) | N | N | 9.8 |
| Aflibercept | G1 | VEGF R1 + R2 | N | N | n/a |
| Dulaglutide | G4 (mut) | GLP1 | N | Y | 3.7 |
| Eloctate | G1 | FVIII | N | N | 0.8 |
| Alprolix | G1 | FIX | N | N | 3.6 |

TABLE II

Table II. Affinity of IL-2 Fc fusion proteins for IL2RA and IL2RB subunits

| Ligand | Analyte | Method | $k_{on}$ | $k_{off}$ | $K_d$ (M) |
|---|---|---|---|---|---|
| IL2RA | IL-2 | Kinetic | $5.85 \times 10^6$ | $8.4 \times 10^{-2}$ | $1.44 \times 10^{-8}$ |
|  | N88RL9AG1 | Kinetic | $1.78 \times 10^6$ | $1.0 \times 10^{-2}$ | $5.63 \times 10^{-9}$ |
|  | D20HL0G2 | Kinetic | $1.66 \times 10^7$ | 0.137 | $8.30 \times 10^{-9}$ |
|  | IL-2 | Equilibrium | — | — | $1.47 \times 10^{-8}$ |
|  | N88RL9AG1 | Equilibrium | — | — | $9.36 \times 10^{-9}$ |
| IL2RB | IL-2 | Kinetic | $5.10 \times 10^5$ | $3.0 \times 10^{-1}$ | $5.87 \times 10^{-7}$ |
|  | N88RL9AG1 | Kinetic | nd | nd | — |
|  | IL-2 | Equilibrium | — | — | $2.53 \times 10^{-7}$ |
|  | N88RL9AG1 | Equilibrium | — | — | $7.60 \times 10^{-2}$ | nd: binding not detected

TABLE III

| Protein | IL2 | Peptide Linker | Configuration | SEQ ID # |
|---|---|---|---|---|
| N88RL0AG1 | N88R | 0 | X-Fc | 6 |
| N88RL5AG1 | N88R | 5 | X-Fc | 7 |
| N88RL10AG1 | N88R | 10 | X-Fc | 8 |
| N88RL15AG1 | N88R | 15 | X-Fc | 9 |
| N88RL20AG1 | N88R | 20 | X-Fc | 10 |
| WTL0AG1 | wt | 0 | X-Fc | 11 |
| WTL15AG1 | wt | 15 | X-Fc | 12 |
| D20HL15AG1 | D20H | 15 | X-Fc | 13 |
| AG1L15D20H | D20H | 15 | Fc-X | 14 |

TABLE IV

| Protein | EC50 | Maximal pSTAT5 response at $10^{-8}$ M | Fold increase in maximal pSTAT5 response |
|---|---|---|---|
| N88RL0AG1 | $>10^{-8}$ | 0.33 | 1.0 |
| N88RL5AG1 | $>10^{-8}$ | 0.52 | 1.6 |
| N88RL9AG1 | $7 \times 10^{-10}$ | 0.96 | 2.9 |
| N88RL10AG1 | $9 \times 10^{-10}$ | 0.90 | 2.7 |
| N88RL15AG1 | $4 \times 10^{-10}$ | 1.22 | 3.7 |
| N88RL20AG1 | $1 \times 10^{-10}$ | 1.40 | 4.2 |

TABLE V

| | Control | IL-2 | WTL15AG1 | N88R/IL2 | N88RL15AG1 |
|---|---|---|---|---|---|
| Treg cells | 0.8 | 99.9 | 99.8 | 99.9 | 75.1 |
| Activated CD4 Teff cells | 0.1 | 70.5 | 65.2 | 3.7 | 0.1 |
| CD4 Teff cells | 0.2 | 60.9 | 40.0 | 2.4 | 0.5 |
| CD8 Teff cells | 0.1 | 90.2 | 35.4 | 2.3 | 0.1 |
| NKT cells | 0.5 | 74.9 | 60.5 | 20.5 | 5.2 |
| NK cells | 0.3 | 96.8 | 96.1 | 49.9 | 19.3 |
| B cells | 0.1 | 20.9 | 10.6 | 0.2 | 0.1 |

Percentage of pSTAT5+ cells in 7 immune cells types in human PBMC.

Cells were treated with proteins indicated in the column headings and analyzed as described in Example 6.

TABLE VI

| Protein | IL2 | Peptide Linker (aa) | Fusion Partner | SEQ ID # |
|---|---|---|---|---|
| N88RL25AG1 | N88R | 0 | IgG1 Fc N297A | 20 |
| N88RL30AG1 | N88R | 5 | IgG1 Fc N297A | 21 |
| N88RL15G1ED | N88R | 10 | IgG1 Fc | 22 |
| N88RL15G2 | N88R | 15 | IgG2 Fc | 23 |
| N88RL15G4(S228P) | N88R | 20 | IgG4 Fc | 24 |
| N88RL15HSA | wt | 0 | HSA | 25 |
| HSAL15N88R | wt | 15 | HSA | 26 |
| N88IL15AG1 | N88I | 15 | IgG1 Fc N297A | 27 |
| N88GL15AG1 | N88G | 15 | IgG1 Fc N297A | 28 |
| Q126FL15AG1 | Q126F | 15 | IgG1 Fc N297A | 29 |
| Q126LL15AG1 | Q126L | 15 | IgG1 Fc N297A | 30 |
| N88RT3AK15AG1 | N88R, T3A | 15 | IgG1 Fc N297A | 31 |

TABLE VII

| Protein | EC50 | Maximal pSTAT5 response at $10^{-8}$ M (% pSTAT5+ cells) | pSTAT5 response at $10^{-8}$ M (% of wt IL-2 response) |
|---|---|---|---|
| N88RL15AG1 | $13.0 \times 10^{-10}$ | 1.12 | 73 |
| N88RL20AG1 | $9.5 \times 10^{-10}$ | 1.18 | 77 |
| N88RL25AG1 | $29.7 \times 10^{-10}$ | 1.10 | 71 |
| N88RL30AG1 | $8.5 \times 10^{-10}$ | 1.18 | 77 |

TABLE VIII

| Protein | EC50 | Maximal pSTAT5 response at $10^{-8}$ M (% pSTAT5+ cells) | pSTAT5 response at $10^{-8}$ M (% of wt IL-2 response) |
|---|---|---|---|
| N88RL15G1ED | $5.2 \times 10^{-9}$ | 0.90 | 58 |
| N88RL15G2 | — | 0.71 | 46 |
| N88RL15G4(S228P) | $6.9 \times 10^{-9}$ | 0.77 | 50 |
| N88RL15HSA | — | 0.32 | 21 |
| HSAL15N88R | — | 0.68 | 44 |

TABLE IX

| Protein | EC50 | Maximal pSTAT5 response at $10^{-8}$ M (% pSTAT5+ cells) | pSTAT5 response at $10^{-8}$ M (% of wt IL-2 response) |
|---|---|---|---|
| N88IL15AG1 | — | 0.00 | 0 |
| N88GL15AG1 | $8.1 \times 10^{-10}$ | 0.81 | 53 |
| Q126FL15AG1 | $9.1 \times 10^{-10}$ | 0.75 | 49 |
| Q126LL15AG1 | $9.5 \times 10^{-10}$ | 1.66 | 108 |
| N88RT3AK15AG1 | $1.9 \times 10^{-9}$ | 0.97 | 63 |

SEQUENCE LISTINGS

SEQ ID NO. 1
>human IL-2(N88R)
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFCQSIISTLT SEQ ID NO. 2
>human IgG1 (N297A) Fc
DKTHTCPPCPAPELLGGPSVFLFPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEALHNHYTQKSLSLSP
GK SEQ ID NO. 3
>human IgG2 Fc
VECPPCPAPPVAGPSVFLFPPKPKDTLMISRTPEVTCVVVDVSHEDPEVQFNWYVDGVEVHNAKTKPREEQFNST
FRVVSVLTVVHQDWLNGKEYKCKVSNKGLPAPIEKTISKTKGQPREPQVYLTPPSREEMTKNQVSLTCLVKGFYP
SDIAVEWESNGQPENNYKTTPPMLDSDGSFFLYSKLTVDKSRWQQGNVFSCSVMHEALHNHYTQKSLSLSPGK*

SEQ ID NO. 4
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFCQSIISTLTGGGGAGGGGDKTHTCPP
CPAPELLGGPSVFLFPPKPKDTLMISRTPEVTCVVVDVSHEDPEVKFNWYVDGVEVHNAKTKPREEQYASTYRVV
SVLTVLHQDWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLSLSPGK*

SEQ ID NO. 5
>D20HL0G2
APTSSSTKKTQLQLEHLLLHLQMILNGINNYKNPKLTRMLTFKFYMPKKATELKHLQCLEEELKPLEEVLNLAQS
KNFHLRPRDLISNINVIVLELKGSETTFMCEYADETATIVEFLNRWITFSQSIISTLTVECPPCPAPPVAGPSVF
LFPPKPKDTLMISRTPEVTCVVVDVSHEDPEVQFNWYVDGVEVHNAKTKPREEQFNSTFRVVSVLTVVHQDWLNG

| SEQUENCE LISTINGS |
| --- |
| KEYKCKVSNKGLPAPIEKTISKTKGQPREPQVYTLPPSREEMTKNQVSLTCLVKGFYPSDIAVEWESNGQPENNY
KTTPPMLDSDGSFFLYSKLTVDKSRWQQGNVFSCSVMHEALHNHYTQKSLSLSPGK*

SEQ ID NO. 6
>N88RL0AG1
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTDKTHTCPPCPAPELLGG
PSVFLFPPYPKDTLMISRTPEVTCVVVDVSHEDPEVKFNWYVDGVEVHANKTKPREEQYASTYRVVSVLTVLHQD
WLNGKEYKCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPG*

SEQ ID NO. 7
>N88RLSAG1
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSDKTHTCPPCPAP
ELLGGPSVFLPPPKPKDTLMISRTPEVTCVVVDVSHEDPEVKFNWYVDGVEVHANKTKPREEQYASTYRVVSVLT
VLHQDWLNGKEYKCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPG*

SEQ ID NO. 8
>N88RL10AG1
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSDKTHTCP
PCPAPELLGGPSVFLFPPPKPKDTLMISRTPEVTCVVVDVSHEDPEVKFNWYVDGVEVHNAKTKPREEQYASTYRV
VSVLTVLHQDWLNGKEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQKSLSLSPG*

SEQ ID NO. 9
>N88RL15AG1
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSDK
THTCPPCPAPELLGGPSVFLFPPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG*

SEQ ID NO. 10
>N88RL20AG1
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSGG
GGSDKTHTCPPCPAPELLGGPSVFLFPPPKPKDTLMISRTPEVTCVVVDVSHEDPEVKFNWYVDGVEVHNAKTKPR
EEQYASTYRVVSVLTVLHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRWQQGNVFSCSVMHEALHNHYTQKSLS
LSPG*

SEQ ID NO. 11
>WTL0AG1
APTSSSTKKTQLQLEHLLLDLQMILNGINNYKNPKLTRMLTFKFYMPKKATELKHLQCLEEELKPLEEVLNLAQS
KNFHLRPRDLISNINVIVLELKGSETTFMCEYADETATIVEFLNRWITFSQSIISTLTDKTHTCPPCPAPELLGG
PSVFLFPPPKPKDTLMISRTPEVTCVVVDVSHEDPEVKFNWYVDGVEVHANKTKPREEQYASTYRVVSVLTVLHQD
WLNGKEYKCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPG*

SEQ ID NO. 12
>WTL15AG1
APTSSSTKKTQLQLEHLLLDLQMILNGINNYKNPKLTRMLTFKFYMPKKATELKHLQCLEEELKPLEEVLNLAQS
KNFHLRPRDLISNINVIVLELKGSETTFMCEYADETATIVEFLNRWITFSQSIISTLTGGGGSGGGGSGGGGSDK
THTCPPCPAPELLGGPSVFLFPPPKPKDTLMISRTPEVTCVVVDVSHEDPEVKFNWYVDGVEVHANKTKPREEQYA
STRYVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG*

SEQ ID NO. 13
>D20HL15AG1
APTSSSTKKTQLQLEHLLLHLQMILNGINNYKNPKLTRMLTFKFYMPKKATELKHLQCLEEELKPLEEVLNLAQS
KNFHLRPRDLISNINVIVLELKGSETTFMCEYADETATIVEFLNRWITFSQSIISTLTGGGGSGGGGSGGGGSDK
THTCPPCPAPELLGGPSVFLFPPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG*

SEQ ID NO. 14
>AG1L15D20H
DKTHTCPPCPAPELLGGPSVFLFPPPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEALHNHYTQKSLSLSP
GGGGGSGGGGSGGGGSAPTSSSTKKTQLQLEHLLLHLQMILNGINNYKNPKLTRMLTFKFYMPKKATELKHLQCL
EEELKPLEEVLNLAQSKNFHLRPRDLISNINVIVLELKGSETTFMCEYADETATIVEFLNRWITFSQSIISTLT* |

SEQUENCE LISTINGS

```
SEQ ID NO. 15
>L9
GGGGAGGGG

SEQ ID NO. 16
>L5
GGGGS

SEQ ID NO. 17
>L10
GGGGSGGGGS

SEQ ID NO. 18
>L15
GGGGSGGGGSGGGGS

SEQ ID NO. 19
>L20
GGGGSGGGGSGGGGSGGGGS

SEQ ID NO. 20
>N88RL25AG1
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSGG
GGSGGGGSDKTHTCPPCPAPELLGGPSVFLFPPKPKDTLMISRTPEVTCVVVDVSHEDPEVKFNWYVDGVEVHNA
KTKPREEQYASTYRVVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVFSCSVMHEALHNHYT
QKSLSLSPG*

SEQ ID NO. 21
>N88RL30AG1
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSGG
GGSGGGGSGGGGSDKTHTCPPCPAPELLGGPSVFLFPPKPKDTLMISRTPEVTCVVVDVSHEDPEVKFNWYVDGV
EVHNAKTKPREEQYASTYRVVSVLTVLHQDWLNGKEYKCKVSNKALPAPIEKTISKAKGQPREYQVYTLPPSRDE
LTKNQVSLTCLVKGFYPSDIAVEWESNGQPENNYKTTPPVLDSDGSFFLYSKLTVDKSRWQQGNVFSCSVMHEAL
HNHYTQKSLSLSPG*

SEQ ID NO. 22
>N88RL3G1ED (E233P/L234A/L235A/G236del)
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSDK
THTCPPCPAPPAAGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVKGFY
PSDIAVEWESNGQEPPNYKTTPPVLDSDGSFFLYSKLTVDKSRWQQGNVFSCSVMHEALHNHYTQKSLSLSPG*

SEQ ID NO. 23
>N88RL3G2
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSVE
CPPCPAPPVAGPSVFLFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKNQVSLTCLVKGFYPSD
ISVEWESNGQPENNYKTTPPMLDSDGSFFLYSKLTVDKSRWQQGNVFSCSVMHEALHNHYTQKSLSLSPG*

SEQ ID NO. 24
>N88RL3G4 (S228P)
APTSSSTKKTQLQLEHLLLDLQMILNGINNYKNPKLTRMLTFKFYMPKKATELHKLQCLEEELKPLEEVLNLAQS
KNFHLRPRDLISRINVIVLELKGSETTFMCEYADETATIVEFLNRWITFSQSIISTLTGGGGSGGGGSGGGGSES
KYGPPCPPCPAPEFLGGPSVFLFPPKPKDTLMISRTPEVTCVVVDVSQEDPEVQFNWYVDGVEVHNAKTKPREEQ
FNSTYRVVSVLTVLHQDWLNGKEYCKCVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEGNVFSCSVMHEALHNHYTQKSLSLSL
G*

SEQ ID NO. 25
>N88RL15HSA
APTSSSTKKTQLQLHELLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSDA
HKSEVAHRFKDLGEENFKALVLIAFAQYLQQCPFEDHVKLVNEVTEFAKTCVADESAENCDKSLHTLFGDKLCTV
ATLRETYGEMADCCAKQEPERNECFLQHKDDNPNLPRLVRPEVDVMCTAFHDNEETFLKKYLYEIARRHPYFYAP
ELLFFAKRYKAAFTECCQAADKAACLLPKLDELRDEGKASSAKQRLKCASLQKFGERAFKAWAVARLSQRFPKAE
FAEVSKLVTDLTKVHTECCHGDLLECADDRADLAKYICENQDSISSKLKECCEKPLLEKSHCIAEVENDEMPADL
PSLAADFVESKDVCKNYAEAKDVFLGMFLYEYARRHPDYSVVLLLRLAKTYETTLEKCCAAADPHECYAKVFDEF
KPLVEEPQNLIKQNCELFEQLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFHADICTLSEKERQIKKQT
ALVELVKHKPKATKEQLKAVMDDFAAFVEKCCKADDKETCFAEEGKKLVAASQAALGL*
```

SEQUENCE LISTINGS

SEQ ID NO. 26
>HSAL15N88R
DAHKSEVAHRFKDLGEENFKALVLIAFAQYLQQCPFEDHVKLVNEVTEFAKTCVADESAENCDKSLHTLFGDKLC
TVATLRETYGEMADCCAKQEPERNECFLQHKDDNPNLPRLVRPEVDVMCTAFHDNEETFLKKYLYEIARRHPYFY
APELLFFAKRYKAAFTECCQAADKAACLLPKLDELRDEGKASSAKQRLKCASLQKFGERAFKAWAVARLSQRFPK
AEFAEVSKLVTDLTKVHTECCHGDLLECADDRADLAKYICENQDSISSKLKECCEKPLLEKSHCIAEVENDEMPA
DLPSLAADFVESKDVCKNYAEAKDVFLGMFLYEYARRHPDYSVVLLLRLAKTYETTLEKCCAAADPHECYAKVFD
EFKPLVEEPQNLIKQNCELFEQLGEYKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPKEFNAETFTFHADICTLSEKERQIKK
QTALVELVKHKPKATKEQLKAVMDDFAAFVEKCCKADDKETCFAEEGKKLVAASQAALGLGGGGSGGGGSGGGGS
APTSSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLT*

SEQ ID NO. 27
>N88IL15AG1
APTSSSTKKTQLQLEHLLLDLQMILNGINNYKNPKLTRMLTFKFYMPKKATELKHLQCLEEELKPLEEVLNLAQS
KNFHLRPRDLISIINVIVLELKGSETTFMCEYADETATIVEFLNRWITFSQSIISTLTGGGGSGGGGSGGGGSDK
THTCPPCPAPELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGP
YPSDIAVEWESNGQPENNYKTTPPVLDSDGSFFLYSKLTVDKSRWQQGNVFSCSVMHEALHNHYTQKSLSLSPG*

SEQ ID NO. 28
>N88GL15AG1
APTSSSTKKTQLQLEHLLLDLQMILNGINNYKNPKLTRMLTFKFYMPKKATELKHLQCLEEELKPLEEVLNLAQS
KNFHLRPRDLISGINVIVLELKGSETTFMCEYADETATIVEFLNRWITFSQSIISTLTGGGGSGGGGSGGGGSDK
THTCPPCPAPELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREYQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG*

SEQ ID NO. 29
>Q126FL15AG1
APTSSSTKKTQLQLEHLLLDLQMILNGINNYKNPKLTRMLTFKFYMPKKATELKHLQCLEEELKPLEEVLNLAQS
KNFHLRPRDLISNINVIVLELKGSETTFMCEYADETATIVEFLNRWITFSFSIISTLTGGGGSGGGGSGGGGSDK
THTCPPCPAPELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG*

SEQ ID NO. 30
>Q126LL15AG1
APTSSSTKKTQLQLEHLLLDLQMILNGINNYKNPKLTRMLTFKFYMPKKATELKHLQCLEEELKPLEEVLNLAQS
KNFHLRPRDLISNINVIVELEKGSETTFMCEYADETATIVEFLNRWITFSLSIISTLTGGGGSGGGGSGGGGSDK
THTCPPCPAPELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG*

SEQ ID NO. 31
>N88RT3AL15AG1
APASSSTKKTQLQLEHLLLDLQMILNGINNYKNPKLTRMLTFKFYMPKKATELKHLQCLEEELKPLEEVLNLAQS
KNFHLRPRDLISRINVIVLELKGSETTFMCEYADETATIVEFLNRWITFSQSIISTLTGGGGSGGGGSGGGGSDK
THTCPPCPAPELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGF
YPSDIAVEWESNGQEPNNYKTTPPVLDSDGSFFLYSKLTVDKSRWQQGNVFSCSVMHEALHNHYTQKSLSLSPG*

The invention claimed is:

1. A fusion protein comprising:
   a. a human IL-2 variant protein domain comprising a C125S substitution relative to SEQ ID NO: 1 and a substitution selected from the group consisting of: N88R, N88G, D20H, Q126L, and Q126F;

b. a peptide linker domain of from 5 to 30 amino acid residues, wherein the peptide linker domain comprises an amino acid sequence selected from the group consisting of SEQ ID NO: 15, SEQ ID NO: 16, SEQ ID NO: 17, SEQ ID NO: 18 and SEQ ID NO: 19; and c. an IgG Fc protein domain, wherein each domain has an amino-terminus (N-terminus) and a carboxy-terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain, wherein protein yield of the fusion protein is increased by at least two-fold relative to a fusion protein that comprises the human IL-2 variant protein domain and the IgG Fc protein domain, but does not comprise the peptide linker domain.

2. The fusion protein of claim 1, wherein the human IL-2 variant protein domain comprises the N88R substitution.

3. The fusion protein of claim 1, wherein the peptide linker domain consists of an amino acid sequence selected from the group consisting of SEQ ID NO: 15, SEQ ID NO: 16, SEQ ID NO: 17, SEQ ID NO: 18 and SEQ ID NO: 19.

4. A dimeric protein comprising two identical chains, wherein each chain comprises a fusion protein comprising:

a. a human IL-2 variant protein domain comprising a C125S substitution relative to SEQ ID NO: 1 and a substitution selected from the group consisting of: N88R, N88G, D20H, Q126L, and Q126F;

b. a peptide linker domain of from 5 to 30 amino acid residues, wherein the peptide linker domain comprises an amino acid sequence selected from the group consisting of SEQ ID NO: 15, SEQ ID NO: 16, SEQ ID NO: 17, SEQ ID NO: 18 and SEQ ID NO: 19; and c. an IgG Fc protein domain, wherein each domain has an amino-terminus (N-terminus) and a carboxy terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain, wherein protein yield of the fusion protein is increased by at least two-fold relative to a fusion protein that comprises the human IL-2 variant protein domain and the IgG Fc protein domain, but does not comprise the peptide linker domain.

5. The dimeric protein of claim 4, wherein the IgG Fc protein domain comprises cysteine residues, and the two identical chains are linked to each other through the cysteine residues of the IgG Fc protein domain.

6. The dimeric protein of claim 4, wherein the human IL-2 variant protein domain comprises the N88R substitution.

7. The dimeric protein of claim 4, wherein the peptide linker domain consists of an amino acid sequence selected from the group consisting of SEQ ID NO: 15, SEQ ID NO: 16, SEQ ID NO: 17, SEQ ID NO: 18 and SEQ ID NO: 19.

8. A pharmaceutical composition comprising a fusion protein comprising:

a. a human IL-2 variant protein domain comprising a C125S substitution relative to SEQ ID NO: 1 and a substitution selected from the group consisting of: N88R, N88G, D20H, Q126L, and Q126F;

b. a peptide linker domain of from 5 to 30 amino acid residues, wherein the peptide linker domain comprises an amino acid sequence selected from the group consisting of SEQ ID NO: 15, SEQ ID NO: 16, SEQ ID NO: 17, SEQ ID NO: 18 and SEQ ID NO: 19; and c. an IgG Fc protein domain, wherein each domain has an amino-terminus (N-terminus) and a carboxy terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain, wherein protein yield of the fusion protein is increased by at least two-fold relative to a fusion protein that comprises the human IL-2 variant protein domain and the IgG Fc protein domain, but does not comprise the peptide linker domain.

9. The pharmaceutical composition of claim 8, wherein the human IL-2 variant protein domain comprises the N88R substitution.

10. The pharmaceutical composition of claim 8, wherein the peptide linker domain consists of an amino acid sequence selected from the group consisting of SEQ ID NO: 15, SEQ ID NO: 16, SEQ ID NO: 17, SEQ ID NO: 18 and SEQ ID NO: 19.

11. A fusion protein comprising an amino acid sequence selected from the group consisting of SEQ ID NO: 4, SEQ ID NO: 7, SEQ ID NO: 8, SEQ ID NO: 9, SEQ ID NO: 10, SEQ ID NO: 20, SEQ ID NO: 21 and SEQ ID NO: 31.

12. A dimeric protein comprising two identical chains, wherein each chain comprises the fusion protein of claim 11.

13. A pharmaceutical composition comprising the fusion protein of claim 11.

* * * * *

SEQUENCE LISTING

<160> NUMBER OF SEQ ID NOS: 31

<210> SEQ ID NO 1
<211> LENGTH: 133
<212> TYPE: PRT
<213> ORGANISM: Artificial Sequence
<220> FEATURE:
<223> OTHER INFORMATION: synthetic peptide - variant IL-2/N88R

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

```
Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 2
<211> LENGTH: 227
<212> TYPE: PRT
<213> ORGANISM: Artificial Sequence
<220> FEATURE:
<223> OTHER INFORMATION: synthetic peptide - human IgG1 Fc N297A

<400> SEQUENCE: 2

Asp Lys Thr His Thr Cys Pro Pro Cys Pro Ala Pro Glu Leu Leu Gly
1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 3
<211> LENGTH: 223
```

<212> TYPE: PRT
<213> ORGANISM: Homo sapiens

<400> SEQUENCE: 3

```
Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65              70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130             135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 4
<211> LENGTH: 369
<212> TYPE: PRT
<213> ORGANISM: Artificial Sequence
<220> FEATURE:
<223> OTHER INFORMATION: synthetic peptide - cDNA-encoded N88RL9AG1

<400> SEQUENCE: 4

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65              70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
```

```
            115                 120                 125
Ile Ser Thr Leu Thr Gly Gly Gly Ala Gly Gly Gly Asp Lys
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Ala Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Asp Glu Leu Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 5
<211> LENGTH: 356
<212> TYPE: PRT
<213> ORGANISM: Artificial Sequence
<220> FEATURE:
<223> OTHER INFORMATION: synthetic peptide - D20HL0G2

<400> SEQUENCE: 5

Ala Pro Thr Ser Ser Thr Lys Lys Thr Gln Leu Gln Leu Glu His
1               5                   10                  15

Leu Leu Leu His Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Ser Ile
            115                 120                 125

Ile Ser Thr Leu Thr Val Glu Cys Pro Pro Cys Pro Ala Pro Pro Val
        130                 135                 140

Ala Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Gln Phe Asn Trp Tyr Val Asp Gly Val Glu
            180                 185                 190

Val His Asn Ala Lys Thr Lys Pro Arg Glu Glu Gln Phe Asn Ser Thr
        195                 200                 205

Phe Arg Val Val Ser Val Leu Thr Val Val His Gln Asp Trp Leu Asn
210                 215                 220

Gly Lys Glu Tyr Lys Cys Lys Val Ser Asn Lys Gly Leu Pro Ala Pro
225                 230                 235                 240

Ile Glu Lys Thr Ile Ser Lys Thr Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Met Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 6
<211> LENGTH: 359
<212> TYPE: PRT
<213> ORGANISM: Artificial Sequence
<220> FEATURE:
<223> OTHER INFORMATION: synthetic peptide - N88RL0AG1

<400> SEQUENCE: 6

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Ser Ile
            115                 120                 125

Ile Ser Thr Leu Thr Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Ala Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly
        355

<210> SEQ ID NO 7
<211> LENGTH: 364
<212> TYPE: PRT
<213> ORGANISM: Artificial Sequence
<220> FEATURE:
<223> OTHER INFORMATION: synthetic peptide - N88RL5AG1

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

Thr Ile Val Glu Phe Leu Asn Arg Trp Ile Thr Phe Ser Gln Ser Ile
            115                 120                 125

Ile Ser Thr Leu Thr Gly Gly Gly Ser Asp Lys Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Ala Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly
        355                 360

<210> SEQ ID NO 8
<211> LENGTH: 369
<212> TYPE: PRT
<213> ORGANISM: Artificial Sequence
<220> FEATURE:
<223> OTHER INFORMATION: synthetic peptide - N88RL10AG1

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Asp Val Ser His Glu
            180                 185                 190

Asp Pro Glu Val Lys Phe Asn Trp Tyr Val Asp Gly Val Glu Val His
            195                 200                 205

Asn Ala Lys Thr Lys Pro Arg Glu Glu Gln Tyr Ala Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
    275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
    355                 360                 365

Gly

<210> SEQ ID NO 9
<211> LENGTH: 374
<212> TYPE: PRT
<213> ORGANISM: Artificial Sequence
<220> FEATURE:
<223> OTHER INFORMATION: synthetic peptide - N88RL15AG1

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95
```

```
Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Gly Ser Gly
        130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
    370

<210> SEQ ID NO 10
<211> LENGTH: 379
<212> TYPE: PRT
<213> ORGANISM: Artificial Sequence
<220> FEATURE:
<223> OTHER INFORMATION: synthetic peptide - N88RL20AG1

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
    130                 135                 140

Gly Gly Gly Ser Gly Gly Gly Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Ala Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly
    370                 375

<210> SEQ ID NO 11
<211> LENGTH: 359
<212> TYPE: PRT
<213> ORGANISM: Homo sapiens

<400> SEQUENCE: 11

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Ala Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly
        355

<210> SEQ ID NO 12
<211> LENGTH: 374
<212> TYPE: PRT
<213> ORGANISM: Homo sapiens

<400> SEQUENCE: 12

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
```

```
            85                  90                  95
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
        130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
                180                 185                 190

Asp Val Ser His Glu Asp Pro Glu Val Lys Phe Asn Trp Tyr Val Asp
                195                 200                 205

Gly Val Glu Val His Asn Ala Lys Thr Lys Pro Arg Glu Glu Gln Tyr
            210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
                260                 265                 270

Glu Pro Gln Val Tyr Thr Leu Pro Pro Ser Arg Asp Glu Leu Thr Lys
            275                 280                 285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly
        370

<210> SEQ ID NO 13
<211> LENGTH: 374
<212> TYPE: PRT
<213> ORGANISM: Artificial Sequence
<220> FEATURE:
<223> OTHER INFORMATION: synthetic peptide - D20HL15AG1

<400> SEQUENCE: 13

Ala Pro Thr Ser Ser Ser Thr Lys Lys Thr Gln Leu Gln Leu Glu His
1               5                   10                  15

Leu Leu Leu His Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
```

```
                65                  70                  75                  80
Arg Pro Arg Asp Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Gln Ser Ile
                115                 120                 125
Ile Ser Thr Leu Thr Gly Gly Gly Ser Gly Gly Gly Ser Gly
                130                 135                 140
Gly Gly Ser Asp Lys Thr His Thr Cys Pro Pro Cys Pro Ala Pro
145                 150                 155                 160
Glu Leu Leu Gly Gly Pro Ser Val Phe Leu Phe Pro Pro Lys Pro Lys
                165                 170                 175
Asp Thr Leu Met Ile Ser Arg Thr Pro Glu Val Thr Cys Val Val Val
                180                 185                 190
Asp Val Ser His Glu Asp Pro Glu Val Lys Phe Asn Trp Tyr Val Asp
                195                 200                 205
Gly Val Glu Val His Asn Ala Lys Thr Lys Pro Arg Glu Glu Gln Tyr
                210                 215                 220
Ala Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
                260                 265                 270
Glu Pro Gln Val Tyr Thr Leu Pro Pro Ser Arg Asp Glu Leu Thr Lys
                275                 280                 285
Asn Gln Val Ser Leu Thr Cys Leu Val Lys Gly Phe Tyr Pro Ser Asp
                290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
                340                 345                 350
Cys Ser Val Met His Glu Ala Leu His Asn His Tyr Thr Gln Lys Ser
                355                 360                 365
Leu Ser Leu Ser Pro Gly
            370

<210> SEQ ID NO 14
<211> LENGTH: 374
<212> TYPE: PRT
<213> ORGANISM: Artificial Sequence
<220> FEATURE:
<223> OTHER INFORMATION: synthetic peptide - AG1L15D20H

<400> SEQUENCE: 14

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                35                  40                  45
Glu Asp Pro Glu Val Lys Phe Asn Trp Tyr Val Asp Gly Val Glu Val
```

```
              50                  55                  60
His Asn Ala Lys Thr Lys Pro Arg Glu Glu Gln Tyr Ala Ser Thr Tyr
 65                  70                  75                  80

Arg Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
        210                 215                 220

Pro Gly Gly Gly Gly Ser Gly Gly Gly Ser Gly Gly Gly Gly
225                 230                 235                 240

Ser Ala Pro Thr Ser Ser Ser Thr Lys Lys Thr Gln Leu Gln Leu Glu
                245                 250                 255

His Leu Leu Leu His Leu Gln Met Ile Leu Asn Gly Ile Asn Asn Tyr
            260                 265                 270

Lys Asn Pro Lys Leu Thr Arg Met Leu Thr Phe Lys Phe Tyr Met Pro
            275                 280                 285

Lys Lys Ala Thr Glu Leu Lys His Leu Gln Cys Leu Glu Glu Glu Leu
        290                 295                 300

Lys Pro Leu Glu Glu Val Leu Asn Leu Ala Gln Ser Lys Asn Phe His
305                 310                 315                 320

Leu Arg Pro Arg Asp Leu Ile Ser Asn Ile Asn Val Ile Val Leu Glu
                325                 330                 335

Leu Lys Gly Ser Glu Thr Thr Phe Met Cys Glu Tyr Ala Asp Glu Thr
            340                 345                 350

Ala Thr Ile Val Glu Phe Leu Asn Arg Trp Ile Thr Phe Ser Gln Ser
            355                 360                 365

Ile Ile Ser Thr Leu Thr
            370

<210> SEQ ID NO 15
<211> LENGTH: 9
<212> TYPE: PRT
<213> ORGANISM: Artificial Sequence
<220> FEATURE:
<223> OTHER INFORMATION: synthetic peptide sequence

<400> SEQUENCE: 15

Gly Gly Gly Gly Ala Gly Gly Gly Gly
 1               5

<210> SEQ ID NO 16
<211> LENGTH: 5
<212> TYPE: PRT
```

```
<213> ORGANISM: Artificial Sequence
<220> FEATURE:
<223> OTHER INFORMATION: synthetic peptide sequence

<400> SEQUENCE: 16

Gly Gly Gly Gly Ser
1               5

<210> SEQ ID NO 17
<211> LENGTH: 10
<212> TYPE: PRT
<213> ORGANISM: Artificial Sequence
<220> FEATURE:
<223> OTHER INFORMATION: synthetic peptide sequence

<400> SEQUENCE: 17

Gly Gly Gly Gly Ser Gly Gly Gly Gly Ser
1               5                   10

<210> SEQ ID NO 18
<211> LENGTH: 15
<212> TYPE: PRT
<213> ORGANISM: Artificial Sequence
<220> FEATURE:
<223> OTHER INFORMATION: synthetic peptide sequence

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: synthetic peptide sequence

<400> SEQUENCE: 19

Gly Gly Gly Gly Ser Gly Gly Gly Gly Ser Gly Gly Gly Gly Ser Gly
1               5                   10                  15

Gly Gly Gly Ser
                20

<210> SEQ ID NO 20
<211> LENGTH: 384
<212> TYPE: PRT
<213> ORGANISM: Artificial Sequence
<220> FEATURE:
<223> OTHER INFORMATION: synthetic peptide - N88RL25AG1

<400> SEQUENCE: 20

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                    85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Gly Ser Gly
130                 135                 140

Gly Gly Gly Ser Gly Gly Gly Gly Ser Gly Gly Gly Ser Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
210                 215                 220

Ala Lys Thr Lys Pro Arg Glu Glu Gln Tyr Ala Ser Thr Tyr Arg Val
225                 230                 235                 240

Val Ser Val Leu Thr Val Leu His Gln Asp Trp Leu Asn Gly Lys Glu
            245                 250                 255

Tyr Lys Cys Lys Val Ser Asn Lys Ala Leu Pro Ala Pro Ile Glu Lys
        260                 265                 270

Thr Ile Ser Lys Ala Lys Gly Gln Pro Arg Glu Pro Gln Val Tyr Thr
            275                 280                 285

Leu Pro Pro Ser Arg Asp Glu Leu Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
            325                 330                 335

Asp Ser Asp Gly Ser Phe Phe Leu Tyr Ser Lys Leu Thr Val Asp Lys
        340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
370                 375                 380

<210> SEQ ID NO 21
<211> LENGTH: 389
<212> TYPE: PRT
<213> ORGANISM: Artificial Sequence
<220> FEATURE:
<223> OTHER INFORMATION: synthetic peptide - N88RL30AG1

<400> SEQUENCE: 21

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

Arg Pro Arg Asp Leu Ile Ser Arg Ile Asn Val Ile Val Leu Glu Leu
            85                  90                  95

Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Ser Gln Ser Ile
    115                 120                 125

Ile Ser Thr Leu Thr Gly Gly Gly Ser Gly Gly Gly Ser Gly
130                 135                 140

Gly Gly Gly Ser Gly Gly Gly Ser Gly Gly Gly Ser Gly Gly
145                 150                 155                 160

Gly Gly Ser Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
    195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Ala
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
370                 375                 380

Ser Leu Ser Pro Gly
385

<210> SEQ ID NO 22
<211> LENGTH: 373
<212> TYPE: PRT
<213> ORGANISM: Artificial Sequence
<220> FEATURE:
<223> OTHER INFORMATION: synthetic peptide - IgG1 Fc
      E233P/L234A/L235A/G236del

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
                50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Asn Val Ile Val Leu Glu Leu
                    85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
130                 135                 140

Gly Gly Ser Asp Lys Thr His Thr Cys Pro Pro Cys Pro Ala Pro
145                 150                 155                 160

Pro Ala Ala Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly
370

<210> SEQ ID NO 23
<211> LENGTH: 370
<212> TYPE: PRT
<213> ORGANISM: Artificial Sequence
<220> FEATURE:
<223> OTHER INFORMATION: synthetic peptide - N88RL3G2

<400> SEQUENCE: 23

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Ser Gly Gly Gly Ser Gly
            130                 135                 140

Gly Gly Ser Val Glu Cys Pro Pro Cys Pro Ala Pro Pro Val Ala
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Gln Phe Asn Trp Tyr Val Asp Gly Val Glu Val
            195                 200                 205

His Asn Ala Lys Thr Lys Pro Arg Glu Glu Gln Phe Asn Ser Thr Phe
 210                 215                 220

Arg Val Val Ser Val Leu Thr Val Val His Gln Asp Trp Leu Asn Gly
225                 230                 235                 240

Lys Glu Tyr Lys Cys Lys Val Ser Asn Lys Gly Leu Pro Ala Pro Ile
                245                 250                 255

Glu Lys Thr Ile Ser Lys Thr Lys Gly Gln Pro Arg Glu Pro Gln Val
            260                 265                 270

Tyr Thr Leu Pro Pro Ser Arg Glu Glu Met Thr Lys Asn Gln Val Ser
            275                 280                 285

Leu Thr Cys Leu Val Lys Gly Phe Tyr Pro Ser Asp Ile Ser Val Glu
 290                 295                 300

Trp Glu Ser Asn Gly Gln Pro Glu Asn Asn Tyr Lys Thr Thr Pro Pro
305                 310                 315                 320

Met Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
 355                 360                 365

Pro Gly
    370

<210> SEQ ID NO 24
<211> LENGTH: 376
<212> TYPE: PRT
<213> ORGANISM: Artificial Sequence
<220> FEATURE:
<223> OTHER INFORMATION: synthetic peptide - IgG4 Fc with hinge mutation
      S228P

<400> SEQUENCE: 24

Ala Pro Thr Ser Ser Ser Thr Lys Lys Thr Gln Leu Gln Leu Glu His

```
1               5                    10                      15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
            50                  55                  60
Pro Leu Glu Glu Val Leu Asn Leu Ala Gln Ser Lys Asn Phe His Leu
65                  70                  75                  80
Arg Pro Arg Asp Leu Ile Ser Arg Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
            115                 120                 125
Ile Ser Thr Leu Thr Gly Gly Gly Gly Ser Gly Gly Gly Ser Gly
            130                 135                 140
Gly Gly Gly Ser Glu Ser Lys Tyr Gly Pro Pro Cys Pro Pro Cys Pro
145                 150                 155                 160
Ala Pro Glu Phe Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser Gln Glu Asp Pro Glu Val Gln Phe Asn Trp Tyr
            195                 200                 205
Val Asp Gly Val Glu Val His Asn Ala Lys Thr Lys Pro Arg Glu Glu
210                 215                 220
Gln Phe Asn Ser Thr Tyr Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Gly Leu Pro Ser Ser Ile Glu Lys Thr Ile Ser Lys Ala Lys Gly Gln
            260                 265                 270
Pro Arg Glu Pro Gln Val Tyr Thr Leu Pro Pro Ser Gln Glu Glu Met
            275                 280                 285
Thr Lys Asn Gln Val Ser Leu Thr Cys Leu Val Lys Gly Phe Tyr Pro
            290                 295                 300
Ser Asp Ile Ala Val Glu Trp Glu Ser Asn Gly Gln Pro Glu Asn Asn
305                 310                 315                 320
Tyr Lys Thr Thr Pro Pro Val Leu Asp Ser Asp Gly Ser Phe Phe Leu
                325                 330                 335
Tyr Ser Arg Leu Thr Val Asp Lys Ser Arg Trp Gln Glu Gly Asn Val
            340                 345                 350
Phe Ser Cys Ser Val Met His Glu Ala Leu His Asn His Tyr Thr Gln
            355                 360                 365
Lys Ser Leu Ser Leu Ser Leu Gly
            370                 375

<210> SEQ ID NO 25
<211> LENGTH: 733
<212> TYPE: PRT
<213> ORGANISM: Artificial Sequence
<220> FEATURE:
<223> OTHER INFORMATION: synthetic peptide - IL2/N88RL15HSA
```

<400> SEQUENCE: 25

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Gly Ser Gly
130                 135                 140

Gly Gly Gly Ser Asp Ala His Lys Ser Glu Val Ala His Arg Phe Lys
145                 150                 155                 160

Asp Leu Gly Glu Glu Asn Phe Lys Ala Leu Val Leu Ile Ala Phe Ala
                165                 170                 175

Gln Tyr Leu Gln Gln Cys Pro Phe Glu Asp His Val Lys Leu Val Asn
            180                 185                 190

Glu Val Thr Glu Phe Ala Lys Thr Cys Val Ala Asp Glu Ser Ala Glu
        195                 200                 205

Asn Cys Asp Lys Ser Leu His Thr Leu Phe Gly Asp Lys Leu Cys Thr
210                 215                 220

Val Ala Thr Leu Arg Glu Thr Tyr Gly Glu Met Ala Asp Cys Cys Ala
225                 230                 235                 240

Lys Gln Glu Pro Glu Arg Asn Glu Cys Phe Leu Gln His Lys Asp Asp
                245                 250                 255

Asn Pro Asn Leu Pro Arg Leu Val Arg Pro Glu Val Asp Val Met Cys
            260                 265                 270

Thr Ala Phe His Asp Asn Glu Glu Thr Phe Leu Lys Lys Tyr Leu Tyr
        275                 280                 285

Glu Ile Ala Arg Arg His Pro Tyr Phe Tyr Ala Pro Glu Leu Leu Phe
290                 295                 300

Phe Ala Lys Arg Tyr Lys Ala Ala Phe Thr Glu Cys Cys Gln Ala Ala
305                 310                 315                 320

Asp Lys Ala Ala Cys Leu Leu Pro Lys Leu Asp Glu Leu Arg Asp Glu
                325                 330                 335

Gly Lys Ala Ser Ser Ala Lys Gln Arg Leu Lys Cys Ala Ser Leu Gln
            340                 345                 350

Lys Phe Gly Glu Arg Ala Phe Lys Ala Trp Ala Val Ala Arg Leu Ser
        355                 360                 365

Gln Arg Phe Pro Lys Ala Glu Phe Ala Glu Val Ser Lys Leu Val Thr
370                 375                 380

Asp Leu Thr Lys Val His Thr Glu Cys Cys His Gly Asp Leu Leu Glu
385                 390                 395                 400

Cys Ala Asp Asp Arg Ala Asp Leu Ala Lys Tyr Ile Cys Glu Asn Gln
                405                 410                 415

```
Asp Ser Ile Ser Ser Lys Leu Lys Glu Cys Cys Glu Lys Pro Leu Leu
                420                 425                 430

Glu Lys Ser His Cys Ile Ala Glu Val Glu Asn Asp Glu Met Pro Ala
            435                 440                 445

Asp Leu Pro Ser Leu Ala Ala Asp Phe Val Glu Ser Lys Asp Val Cys
        450                 455                 460

Lys Asn Tyr Ala Glu Ala Lys Asp Val Phe Leu Gly Met Phe Leu Tyr
465                 470                 475                 480

Glu Tyr Ala Arg Arg His Pro Asp Tyr Ser Val Val Leu Leu Leu Arg
                485                 490                 495

Leu Ala Lys Thr Tyr Glu Thr Thr Leu Glu Lys Cys Cys Ala Ala Ala
            500                 505                 510

Asp Pro His Glu Cys Tyr Ala Lys Val Phe Asp Glu Phe Lys Pro Leu
        515                 520                 525

Val Glu Glu Pro Gln Asn Leu Ile Lys Gln Asn Cys Glu Leu Phe Glu
530                 535                 540

Gln Leu Gly Glu Tyr Lys Phe Gln Asn Ala Leu Leu Val Arg Tyr Thr
545                 550                 555                 560

Lys Lys Val Pro Gln Val Ser Thr Pro Thr Leu Val Glu Val Ser Arg
                565                 570                 575

Asn Leu Gly Lys Val Gly Ser Lys Cys Cys Lys His Pro Glu Ala Lys
            580                 585                 590

Arg Met Pro Cys Ala Glu Asp Tyr Leu Ser Val Val Leu Asn Gln Leu
        595                 600                 605

Cys Val Leu His Glu Lys Thr Pro Val Ser Asp Arg Val Thr Lys Cys
610                 615                 620

Cys Thr Glu Ser Leu Val Asn Arg Arg Pro Cys Phe Ser Ala Leu Glu
625                 630                 635                 640

Val Asp Glu Thr Tyr Val Pro Lys Glu Phe Asn Ala Glu Thr Phe Thr
                645                 650                 655

Phe His Ala Asp Ile Cys Thr Leu Ser Glu Lys Glu Arg Gln Ile Lys
            660                 665                 670

Lys Gln Thr Ala Leu Val Glu Leu Val Lys His Lys Pro Lys Ala Thr
        675                 680                 685

Lys Glu Gln Leu Lys Ala Val Met Asp Asp Phe Ala Ala Phe Val Glu
690                 695                 700

Lys Cys Cys Lys Ala Asp Asp Lys Glu Thr Cys Phe Ala Glu Glu Gly
705                 710                 715                 720

Lys Lys Leu Val Ala Ala Ser Gln Ala Ala Leu Gly Leu
                725                 730

<210> SEQ ID NO 26
<211> LENGTH: 733
<212> TYPE: PRT
<213> ORGANISM: Artificial Sequence
<220> FEATURE:
<223> OTHER INFORMATION: synthetic peptide - IL2/HSAL15N88R

<400> SEQUENCE: 26

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45
```

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
                580                 585                 590

Gly Gly Ser Gly Gly Gly Ser Ala Pro Thr Ser Ser Ser Thr Lys
            595                 600                 605

Lys Thr Gln Leu Gln Leu Glu His Leu Leu Leu Asp Leu Gln Met Ile
            610                 615                 620

Leu Asn Gly Ile Asn Asn Tyr Lys Asn Pro Lys Leu Thr Arg Met Leu
625                 630                 635                 640

Thr Phe Lys Phe Tyr Met Pro Lys Lys Ala Thr Glu Leu Lys His Leu
                645                 650                 655

Gln Cys Leu Glu Glu Glu Leu Lys Pro Leu Glu Glu Val Leu Asn Leu
                660                 665                 670

Ala Gln Ser Lys Asn Phe His Leu Arg Pro Arg Asp Leu Ile Ser Arg
                675                 680                 685

Ile Asn Val Ile Val Leu Glu Leu Lys Gly Ser Glu Thr Thr Phe Met
            690                 695                 700

Cys Glu Tyr Ala Asp Glu Thr Ala Thr Ile Val Glu Phe Leu Asn Arg
705                 710                 715                 720

Trp Ile Thr Phe Ser Gln Ser Ile Ile Ser Thr Leu Thr
                725                 730

<210> SEQ ID NO 27
<211> LENGTH: 374
<212> TYPE: PRT
<213> ORGANISM: Artificial Sequence
<220> FEATURE:
<223> OTHER INFORMATION: synthetic peptide - N88IL15AG1

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Ile Ile Asn Val Ile Val Leu Glu Leu
                85                  90                  95

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Gly Ser Gly
    130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
    370

<210> SEQ ID NO 28
<211> LENGTH: 374
<212> TYPE: PRT
<213> ORGANISM: Artificial Sequence
<220> FEATURE:
<223> OTHER INFORMATION: synthetic peptide - N88GL15AG1

<400> SEQUENCE: 28

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Gly Ile Asn Val Ile Val Leu Glu Leu
                85                  90                  95

Lys Gly Ser Glu Thr Thr Phe Met Cys Glu Tyr Ala Asp Glu Thr Ala
           100                 105                 110

Thr Ile Val Glu Phe Leu Asn Arg Trp Ile Thr Phe Ser Gln Ser Ile
           115                 120                 125

Ile Ser Thr Leu Thr Gly Gly Gly Ser Gly Gly Gly Ser Gly
130                 135                 140

Gly Gly Gly Ser Asp Lys Thr His Thr Cys Pro Cys Pro Ala Pro
145                 150                 155                 160

Glu Leu Leu Gly Gly Pro Ser Val Phe Leu Phe Pro Pro Lys Pro Lys
               165                 170                 175

Asp Thr Leu Met Ile Ser Arg Thr Pro Glu Val Thr Cys Val Val Val
           180                 185                 190

Asp Val Ser His Glu Asp Pro Glu Val Lys Phe Asn Trp Tyr Val Asp
           195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
               245                 250                 255

Pro Ala Pro Ile Glu Lys Thr Ile Ser Lys Ala Lys Gly Gln Pro Arg
           260                 265                 270

Glu Pro Gln Val Tyr Thr Leu Pro Pro Ser Arg Asp Glu Leu Thr Lys
           275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
               325                 330                 335

Lys Leu Thr Val Asp Lys Ser Arg Trp Gln Gln Gly Asn Val Phe Ser
           340                 345                 350

Cys Ser Val Met His Glu Ala Leu His Asn His Tyr Thr Gln Lys Ser
           355                 360                 365

Leu Ser Leu Ser Pro Gly
           370

<210> SEQ ID NO 29
<211> LENGTH: 374
<212> TYPE: PRT
<213> ORGANISM: Artificial Sequence
<220> FEATURE:
<223> OTHER INFORMATION: synthetic peptide - Q126FL15AG1

<400> SEQUENCE: 29

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
               20                  25                  30

Asn Pro Lys Leu Thr Arg Met Leu Thr Phe Lys Phe Tyr Met Pro Lys
           35                  40                  45

Lys Ala Thr Glu Leu Lys His Leu Gln Cys Leu Glu Glu Glu Leu Lys
       50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Phe Ser Ile
        115                 120                 125

Ile Ser Thr Leu Thr Gly Gly Gly Ser Gly Gly Gly Ser Gly
    130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
    195                 200                 205

Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
    370

<210> SEQ ID NO 30
<211> LENGTH: 374
<212> TYPE: PRT
<213> ORGANISM: Artificial Sequence
<220> FEATURE:
<223> OTHER INFORMATION: synthetic peptide - Q126LL15AG1

<400> SEQUENCE: 30

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

Asn Pro Lys Leu Thr Arg Met Leu Thr Phe Lys Phe Tyr Met Pro Lys
 35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
             100                 105                 110

Thr Ile Val Glu Phe Leu Asn Arg Trp Ile Thr Phe Ser Leu Ser Ile
         115                 120                 125

Ile Ser Thr Leu Thr Gly Gly Gly Ser Gly Gly Gly Ser Gly
     130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                 165                 170                 175

Asp Thr Leu Met Ile Ser Arg Thr Pro Glu Val Thr Cys Val Val Val
             180                 185                 190

Asp Val Ser His Glu Asp Pro Glu Val Lys Phe Asn Trp Tyr Val Asp
         195                 200                 205

Gly Val Glu Val His Asn Ala Lys Thr Lys Pro Arg Glu Glu Gln Tyr
     210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                 245                 250                 255

Pro Ala Pro Ile Glu Lys Thr Ile Ser Lys Ala Lys Gly Gln Pro Arg
             260                 265                 270

Glu Pro Gln Val Tyr Thr Leu Pro Pro Ser Arg Asp Glu Leu Thr Lys
         275                 280                 285

Asn Gln Val Ser Leu Thr Cys Leu Val Lys Gly Phe Tyr Pro Ser Asp
     290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                 325                 330                 335

Lys Leu Thr Val Asp Lys Ser Arg Trp Gln Gln Gly Asn Val Phe Ser
             340                 345                 350

Cys Ser Val Met His Glu Ala Leu His Asn His Tyr Thr Gln Lys Ser
         355                 360                 365

Leu Ser Leu Ser Pro Gly
     370

<210> SEQ ID NO 31
<211> LENGTH: 374
<212> TYPE: PRT
<213> ORGANISM: Artificial Sequence
<220> FEATURE:
<223> OTHER INFORMATION: synthetic peptide - N88RT3AL15AG1

```
<400> SEQUENCE: 31

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr Gly Gly Gly Gly Ser Gly Gly Gly Gly Ser Gly
130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
            210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
            275                 280                 285

Asn Gln Val Ser Leu Thr Cys Leu Val Lys Gly Phe Tyr Pro Ser Asp
        290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
            370
```